United States Patent
Gross et al.

(10) Patent No.: US 9,650,405 B2
(45) Date of Patent: May 16, 2017

(54) MODIFIED SOPHOROLIPIDS AS OIL SOLUBILIZING AGENTS

(71) Applicant: Polytechnic Institute of New York University, Brooklyn, NY (US)

(72) Inventors: Richard A. Gross, Plainview, NY (US); Thavasi Rengathavasi, Bayside, WI (US); Amanda Koh, Brooklyn, NY (US); Yifeng Peng, Brooklyn, NY (US)

(73) Assignee: Synthezyme, LLC, Rensselaer, NY (US)

( * ) Notice: Subject to any disclaimer, the term of this patent is extended or adjusted under 35 U.S.C. 154(b) by 0 days.

(21) Appl. No.: 13/902,879

(22) Filed: May 27, 2013

(65) Prior Publication Data

US 2013/0331466 A1    Dec. 12, 2013

Related U.S. Application Data

(63) Continuation-in-part of application No. 13/080,609, filed on Apr. 5, 2011, now Pat. No. 8,685,942.

(60) Provisional application No. 61/320,885, filed on Apr. 5, 2010.

(51) Int. Cl.

| A01N 43/16 | (2006.01) |
| A01N 43/90 | (2006.01) |
| A01N 25/30 | (2006.01) |
| A61Q 1/00 | (2006.01) |
| C12P 19/44 | (2006.01) |
| A61K 31/739 | (2006.01) |
| C07H 15/04 | (2006.01) |
| A61Q 9/02 | (2006.01) |
| A61Q 1/06 | (2006.01) |
| A61Q 5/12 | (2006.01) |
| C11D 3/22 | (2006.01) |
| A61K 8/60 | (2006.01) |
| A61Q 19/00 | (2006.01) |
| A61K 31/7028 | (2006.01) |
| A61Q 11/00 | (2006.01) |
| A61Q 1/10 | (2006.01) |
| A61Q 5/02 | (2006.01) |
| A61Q 19/10 | (2006.01) |
| A61Q 17/00 | (2006.01) |

(52) U.S. Cl.
CPC .............. *C07H 15/04* (2013.01); *A01N 25/30* (2013.01); *A61K 8/602* (2013.01); *A61K 31/7028* (2013.01); *A61Q 1/00* (2013.01); *A61Q 1/06* (2013.01); *A61Q 5/12* (2013.01); *A61Q 9/02* (2013.01); *A61Q 19/00* (2013.01); *C11D 3/22* (2013.01); *A61K 2800/10* (2013.01); *A61Q 1/10* (2013.01); *A61Q 5/02* (2013.01); *A61Q 11/00* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| 5,756,471 | A  | * | 5/1998 | Hillion et al. | .............. | 514/25 |
| 6,261,575 | B1 | * | 7/2001 | Hoppe et al. | .............. | 424/401 |
| 2010/0004472 | A1 | * | 1/2010 | Kitagawa et al. | ............ | 549/417 |

OTHER PUBLICATIONS

Zhang, "Synthesis and interfacial properties of sophorolipid derivatives", Colloids and Surfaces A: Physicochem. Eng. Aspects, 240, 75-82, 2004.*
Singh, "Regioselective Enzyme-Catalyzed Synthesis of Sophorolipid Esters, Amides, and Multifunctional Monomers", J. Org. Chem. 2003, 68, 5466-5477.*
Zhang, "Synthesis and interfacial properties of sophorolipid derivatives", Colloids and Surfaces A: Physicochem. Eng. Aspects 240 (2004) 75-82.*
Bisht, "Enzyme-Mediated Regioselective Acylations of Sophorolipids", J. Org. Chem. 1999, 64, 780-789.*

* cited by examiner

*Primary Examiner* — Robert T Crow
*Assistant Examiner* — John P Nguyen
(74) *Attorney, Agent, or Firm* — Laurence P. Colton; Smith Tempel Blaha LLC

(57) ABSTRACT

A method for the development of a library of modified sophorolipids using a wide-range of chemical and enzyme catalyst tools to identify modified sophorolipids that can be used in pure form, as mixtures with other modified sophorolipids, as mixtures with natural sophorolipids, as mixtures with modified and natural sophorolipids, and as mixtures with other compounds known by one skilled in the art for use in the dispersion, solubilization or emulsification of various oil types and nutraceuticals, and modified sophorolipids for use in dispersion, solubilization or emulsification processes.

17 Claims, 21 Drawing Sheets

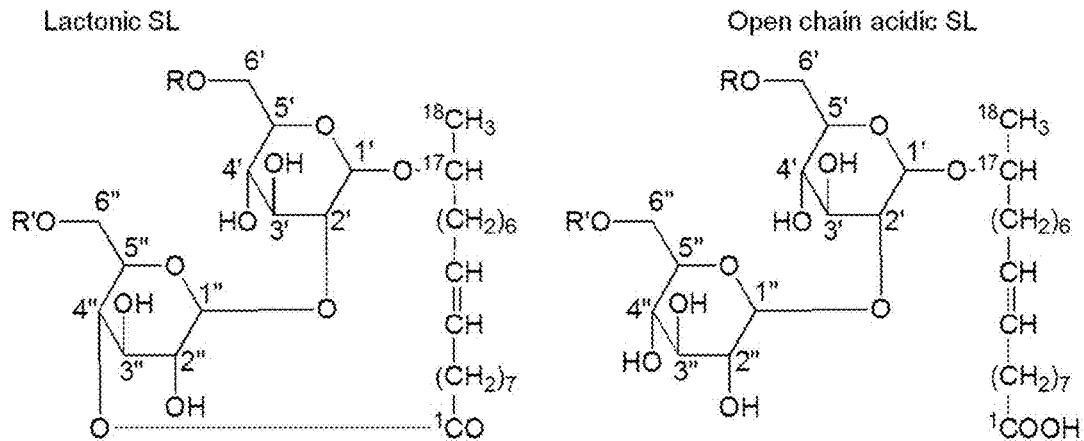
FIG. 1. Structure of lactonic and acidic forms of sophorolipid mixture (Compound 1) produced by *Candida bombicola* (R = COCH$_3$ and/or H).
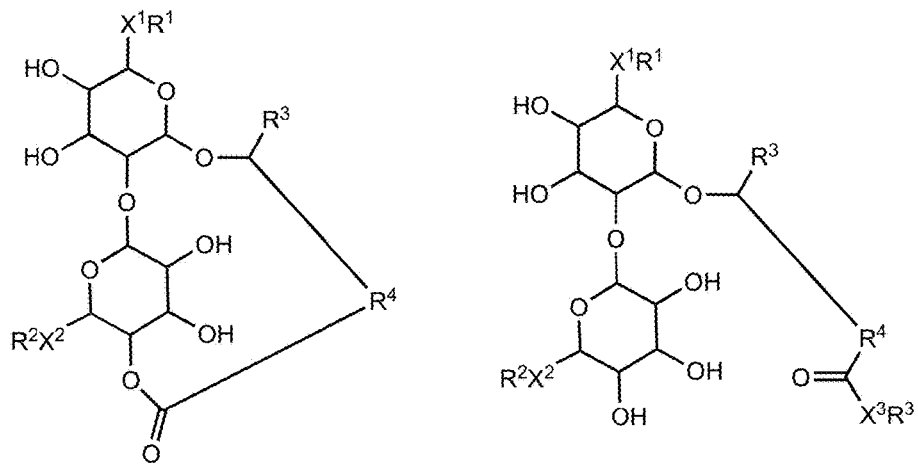
FIG. 2: General formulas for sophorolipids and sophorolipid analogs of the present invention.

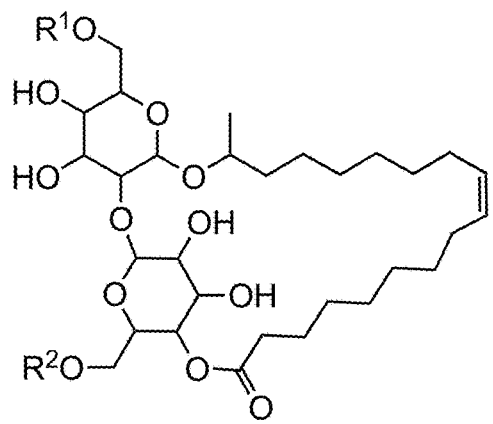
FIG. 3: Natural sophorolipids in the lactonic form (Compound 2)
$R^1$ = H, Ac
$R^2$ = H, Ac
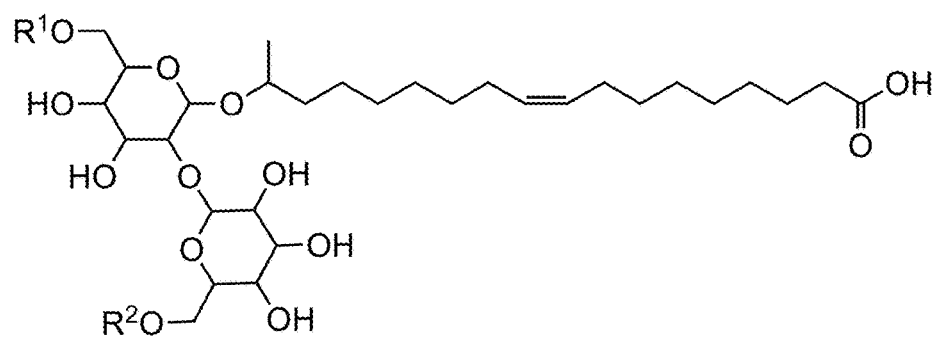
FIG. 4. Natural sophorolipids in the open chain (acidic) form (Compound 3).
3 mixture of
$R^1 = R^2 = Ac$
$R^1 = Ac; R^2 = H$
$R^1 = H; R^2 = Ac$
$R^1 = R^2 = H$

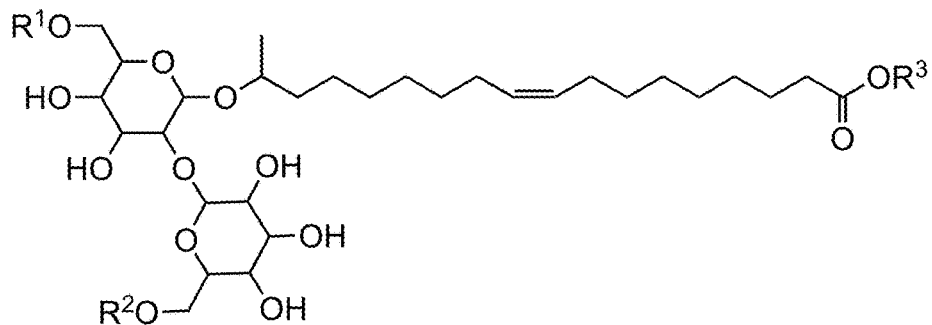
FIG. 5. Representative ester derivatives of the open chain form.
| | |
|---|---|
| 6 | $R^1 = R^2 = H; R^3 = Me$ |
| 7 | $R^1 = R^2 = H; R^3 = Et$ |
| 8 | $R^1 = R^2 = H; R^3 = Bu$ |
| 9 | $R^1 = Ac; R^2 = H; R^3 = Et$ |
| 10 | $R^1 = R^2 = Ac; R^3 = Et$ |
| 11 | $R^1 = H; R^2 = Ac; R^3 = Bu$ |
| 12 | $R^1 = R^2 = Ac; R^3 = Bu$ |
| 13 | $R^1 = H; R^2 = Ac; R^3 = Et$ |
| 14 | $R^1 = R^2 = H; R^3 = Propyl$ |
| 15 | $R^1 = R^2 = H; R^3 = Pentyl$ |
| 16 | $R^1 = H; R^2 = H; R^3 = Hexyl$ |
| 17 | $R^1 = H; R^2 = H; R^3 = Octyl$ |
| 18 | $R^1 = H; R^2 = H; R^3 = Dodecyl$ |

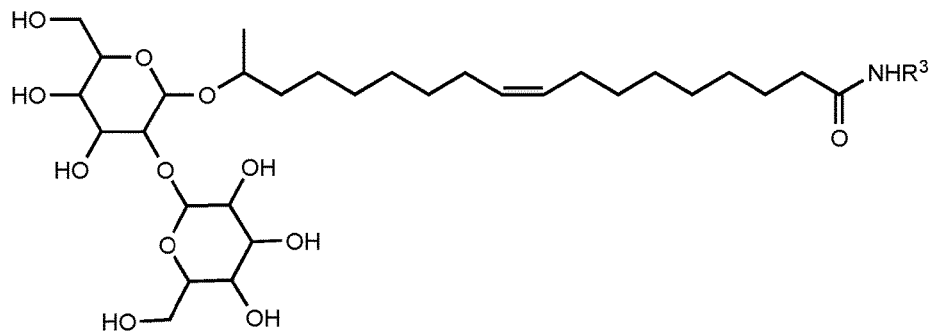

| Compound Code | Sophorolipid amide derivatives – Compounds 19 to 31 |
|---|---|
| 19 | $R^3 = CH_2CH_2OH$ |
| 20 | $R^3 = CH_2CH_2NMe_2$ |
| 21 | $R^3 = CH_2CH_2NMe_3^+I^-$ |
| 22 | $R^3 = CH_3$ |
| 23 | $R^3 = CH_2CH_3$ |
| 24 | $R^3 = (CH_2)_3CH_3$ |
| 25 | $R^3 = (CH_2)_5CH_3$ |
| 26 | $R^3 = (CH_2)_7CH_3$ |
| 27 | $R^3 = CH_2CH_2SH$ |
| 28 | $R^3 = CH_2CH_2$-(1-pyrrolidinyl) |
| 29 | $R^3 = CH_2CH_2$-(2-imidazolyl) |
| 30 | saturated lipid moiety, $R^3 = CH_2CH_2NMe_2$ |
| 31 | saturated lipid moiety, $R^3 = CH_2CH_2NMe_3^+I^-$ |
| | Sophorolipid biogenic amides - Compounds 32 to 38 |
| 32 | $(CH_2)_5NH_2$ |

FIG. 6A. Amide and related derivatives of the open chain form

| | |
|---|---|
| 33 | $R^3 = (CH_2)_4NH(CH_2)_3NH_2$ |
| 34 | $R^3 = (CH_2)_3NH(CH_2)_4NH\text{-}(CH_2)_3NH_2$ |
| 35 | $R^3 = CH_2CH_2\text{-}(1\text{-Imidazole})$ |
| 36 | $R^3 = CH_2CH_2\text{-}(m,p\text{-benzenediol})$ |
| 37 | $R^3 = CH_2CH_2\text{-}(1\text{-indole})$ |
| 38 | $R^3 = CH_2CH_2\text{-}(p\text{-phenol})$ |

FIG. 6B (continuation of FIG. 6A). Amide and related derivatives of the open chain form

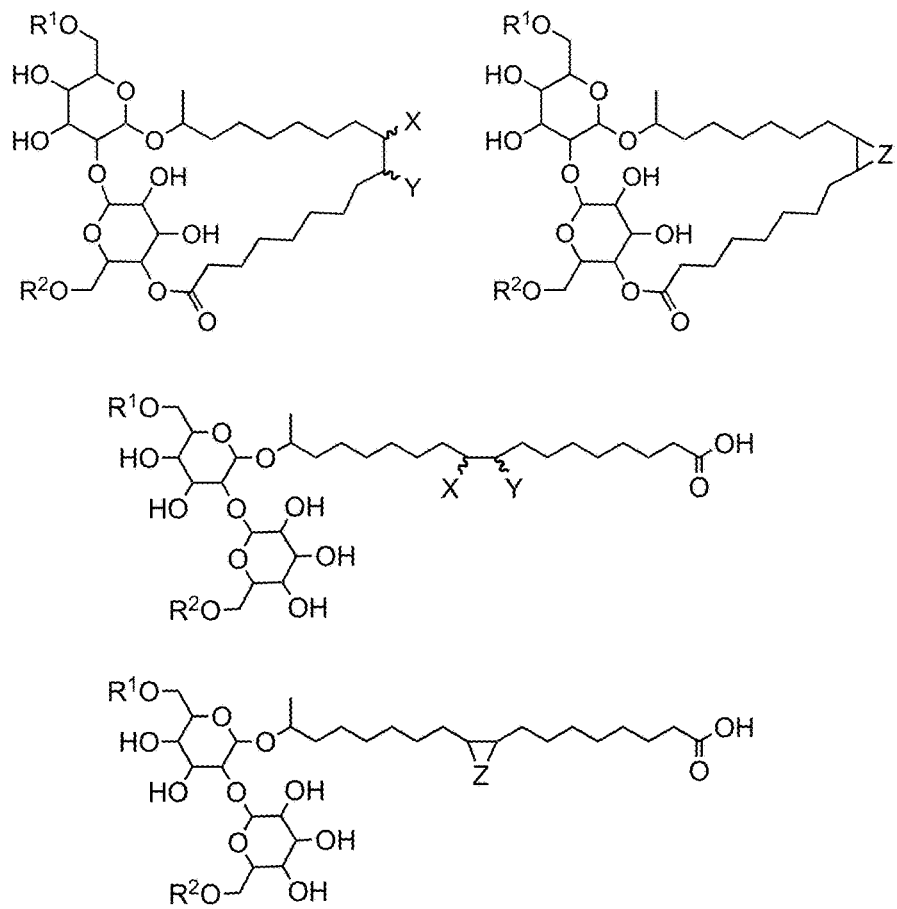
FIG. 7. Derivatives of the C=C (double bond) in the lactonic and open chain forms
X = H, OH, NH$_2$, NHR, SH, SR, OR; Y = H, OH, NH$_2$, NHR, SH, SR, OR
Z = O, NH, NR, S, CHR

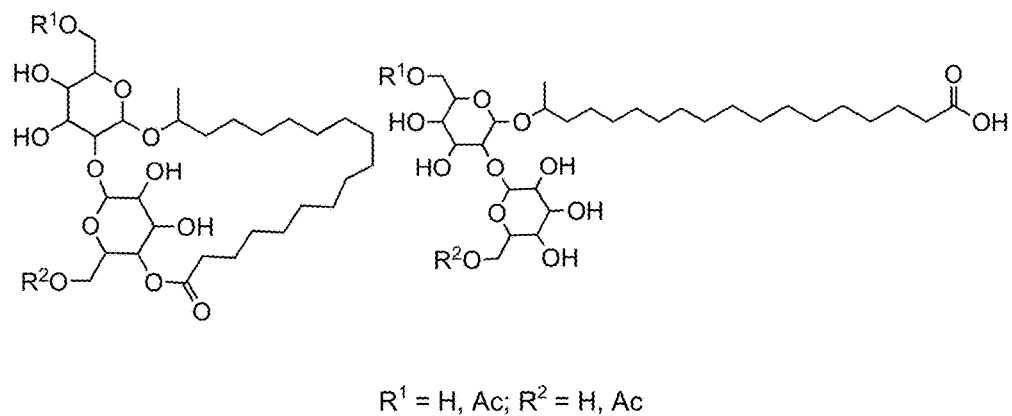
$R^1$ = H, Ac; $R^2$ = H, Ac
FIG. 8. Modified sophorolipids in which the C=C (double bond) in the lactonic and open chain forms have been hydrogenated (hydrogenated natural SLs, Compound 4)
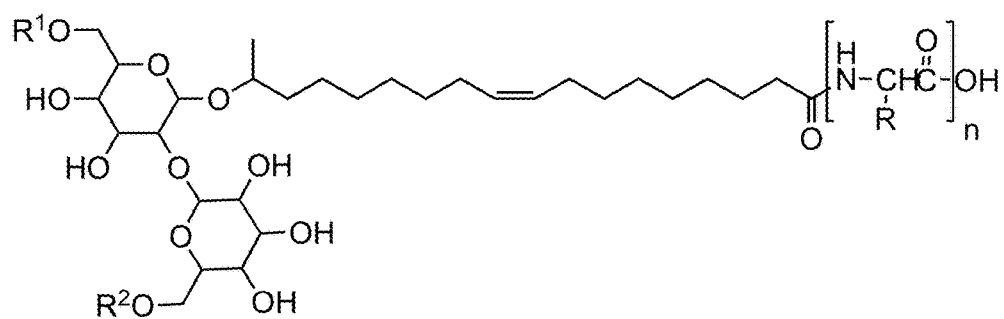
FIG. 9. Peptide derivatives of the open chain form

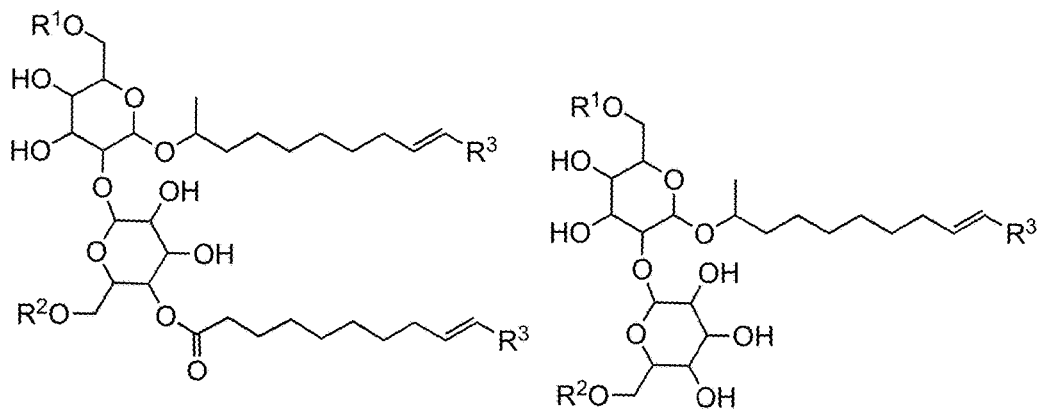
FIG. 10. Trans alkylidenation derivatives of lactonic and open chain SLs
$R^3$ = H, alkyl, aryl, heterocyclic, cationic, anionic groups
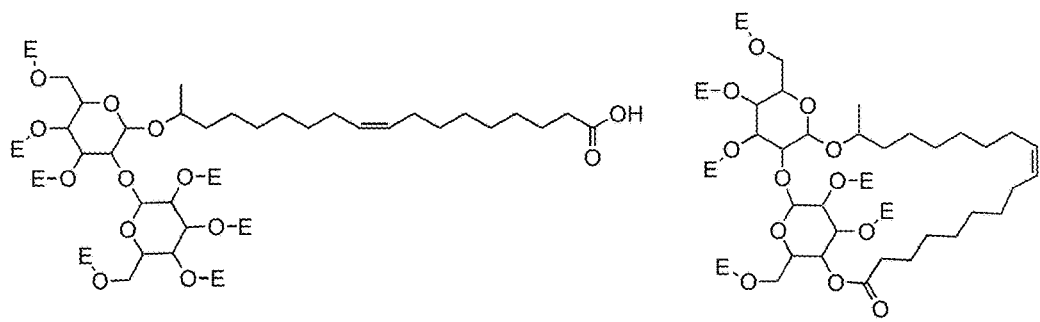
FIG. 11. Electrophile derivatives at sophorose ring
E = $(CH_2\text{-}CH_2O)_nH$, $CH_2\text{-}CH(OH)\text{-}CH_2NMe_3^+$ or $H^+$

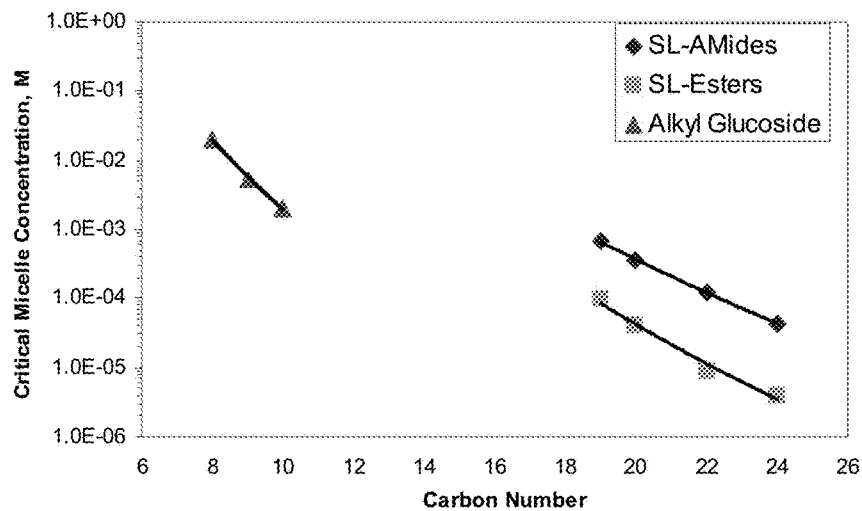
FIG. 12. CMC of SL-amides, SL-esters and alkyl glucoside as a function of alkyl chain length
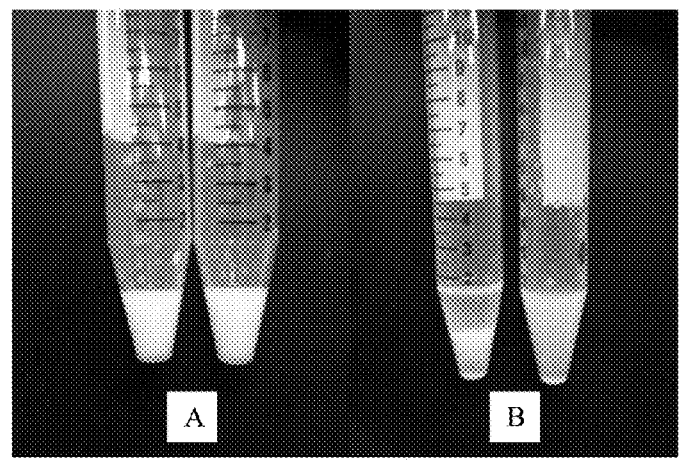
FIG. 13. Dilution test for O/W type emulsions

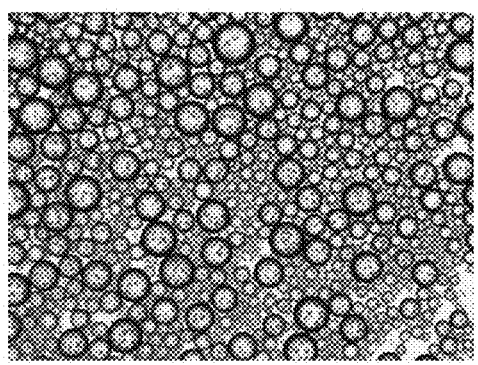 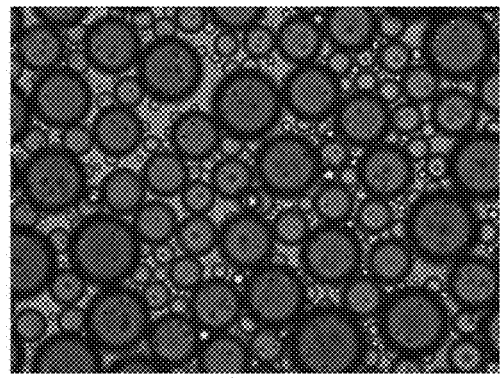
a) Emulsion before dye stained.   b) Emulsion after dye stained by Oil Red O.
FIG. 14. Emulsion with Compound 25 (SL-Hexyl Amide) at 2%, Oil/ Water volume ratio = 7/3.

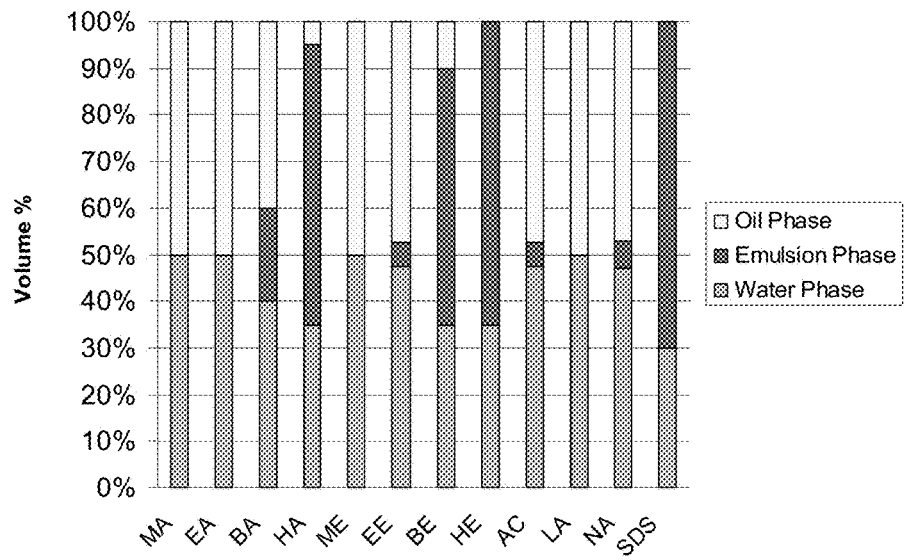

FIG. 15. Emulsion phase separation for emulsions prepared using natural and modified sophorolipids[a] by homogenization of paraffin oil/water (5:5 volume ratio) and 2%-by-weight relative to the water phase[b].

a) MA: SL-Methyl Amide (22); EA: SL-Ethyl Amide (23); BA: SL-Butyl Amide (24); HA: SL-Hexyl Amide (25); ME: SL-Methyl Ester (6); EE: SL-Ethyl Ester (7); BE: SL-Butyl Ester (8); HE: SL-Hexyl Ester (16); AC: Acidic SL (3); LA: Lactonic SL (2); NA: Natural SL (1); SDS: Sodium dodecyl sulfate.

b) Emulsions were prepared by adding 5 mL of paraffin oil into 5 mL of water containing 2%-by-weight of the emulsifier. Then, this mixture was homogenized at 13,000 rpm for 2 minutes. Thereafter, the resulting emulsion was left unagitated at 25°C for 24 hours.

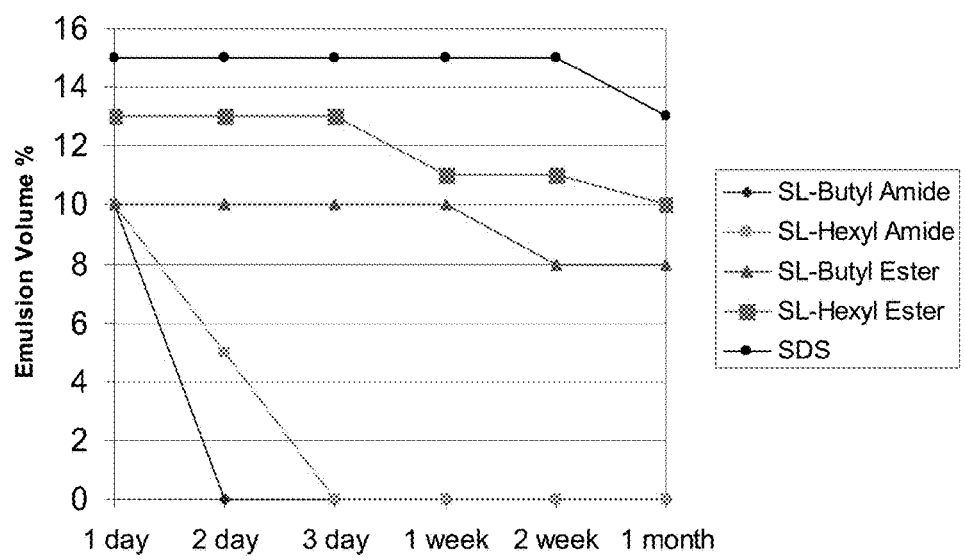
FIG. 16. Emulsion volume percentage change with time at oil/water = 1/9 v/v

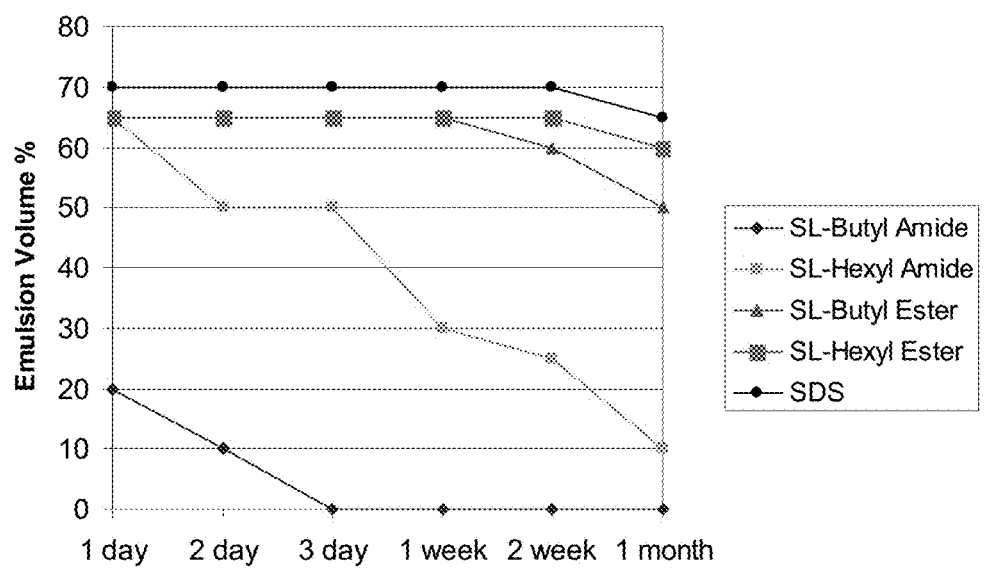
FIG. 17. Emulsion volume percentage change with time at oil/water = 5/5 v/v.

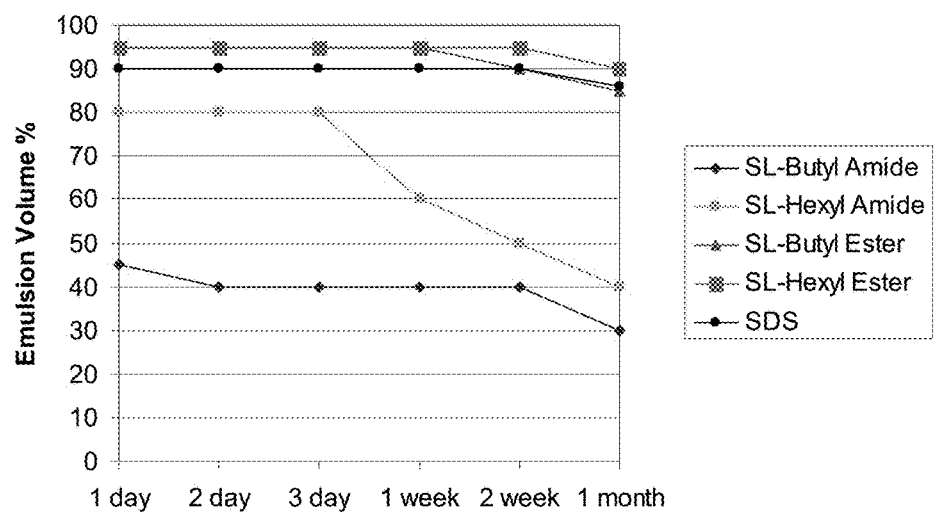
FIG. 18. Emulsion volume percentage change with time at oil/water = 7/3 v/v

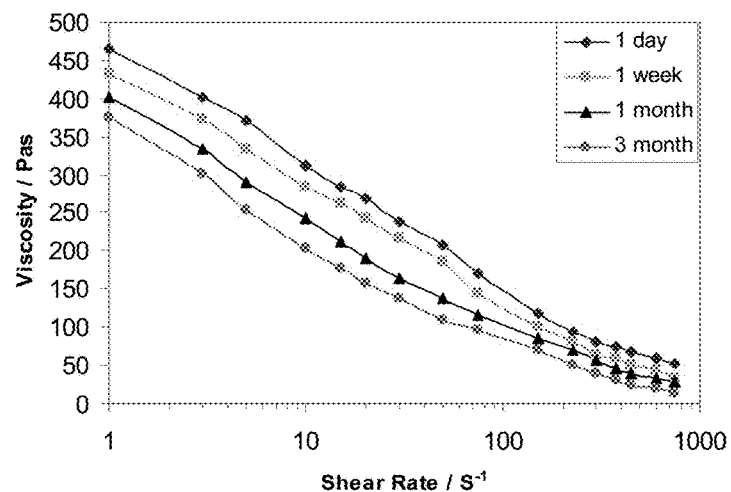
FIG. 19. Emulsion viscosity versus shear rate for oil/water = 7/3 v/v and 2%-by-weight SL-butyl ester (8) relative to paraffin oil.

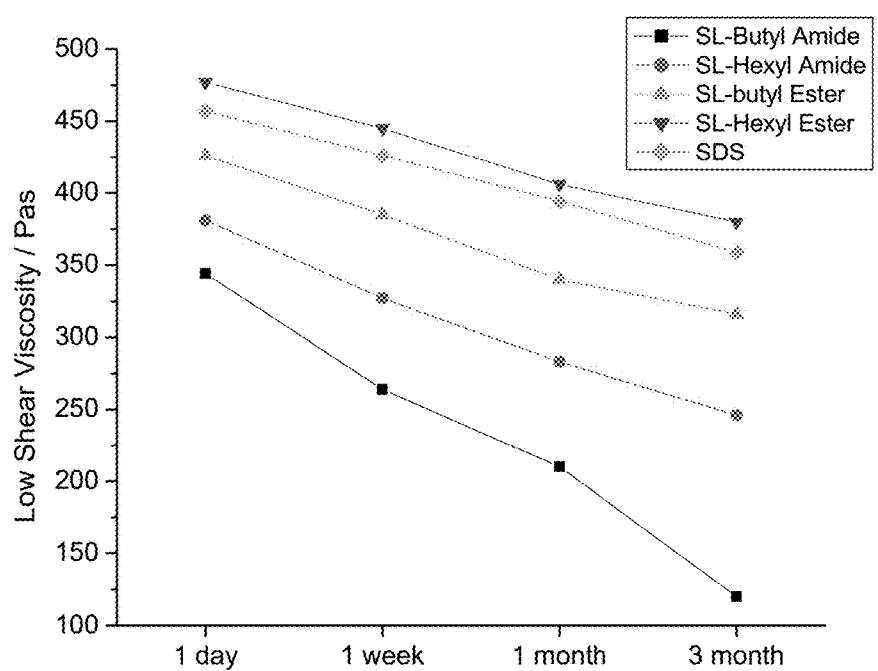
FIG. 20. Viscosity of emulsions prepared from paraffin oil/water 7:3 stabilized by 1%-by-weight MSL or SDS as a function of aging time at room temperature (25°C).

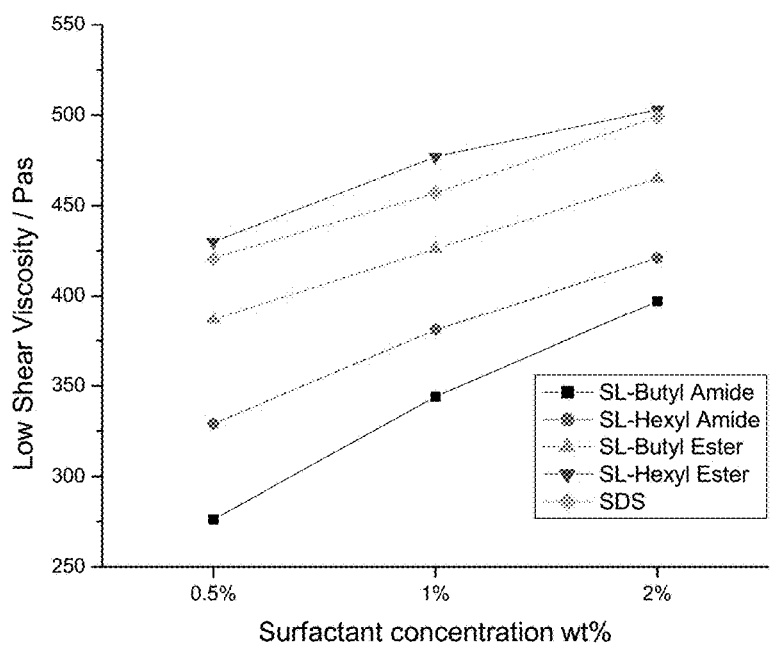
FIG. 21. Viscosity of emulsions prepared from paraffin oil/water 7:3, aged for 24 hours at room temperature (25°C), as a function of MSL or SDS concentration (weight-%-relative to the oil phase)

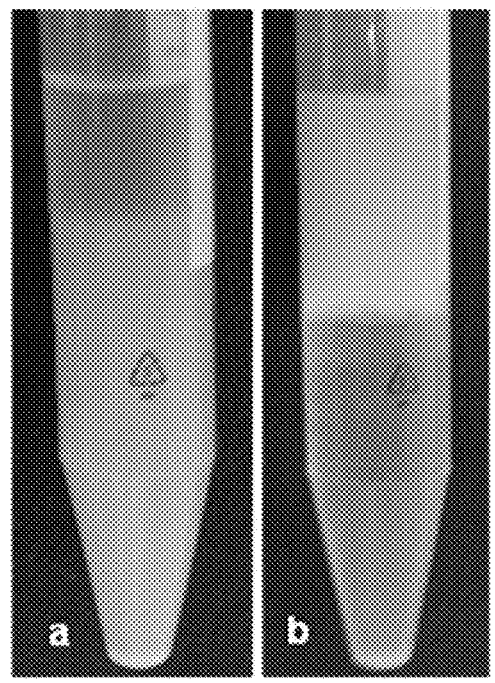
FIG. 22. 1 weight% surfactant, water:paraffin oil= 1:1 (v/v).

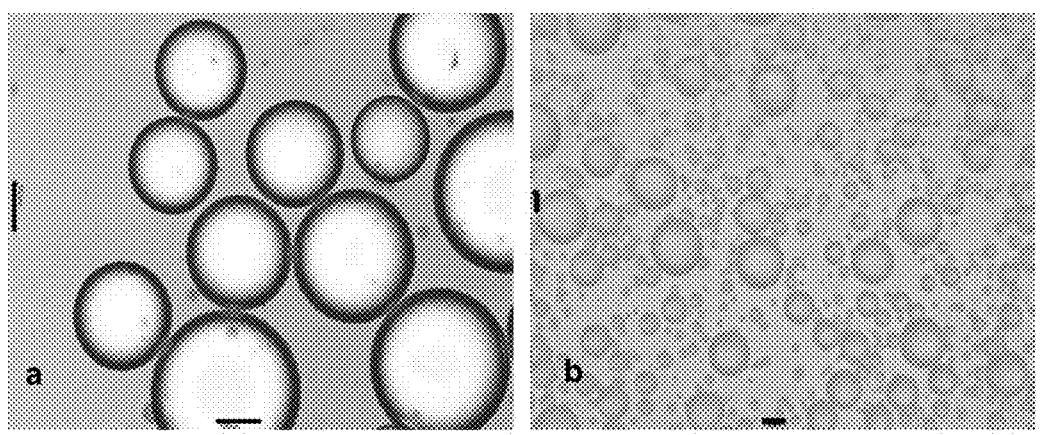
FIG. 23A. Microscopic image of sample A in FIG. 1 diluted in paraffin oil that contained sudan red. The image shows that a water-in-oil emulsion formed (scale bar: 100 μm).
FIG. 23B. Microscopic image of sample B in FIG. 23 diluted in paraffin oil. The water-in-oil emulsion was confirmed by dilution experiment, as dye experiment gave poor resolution (scale bar: 10 μm)

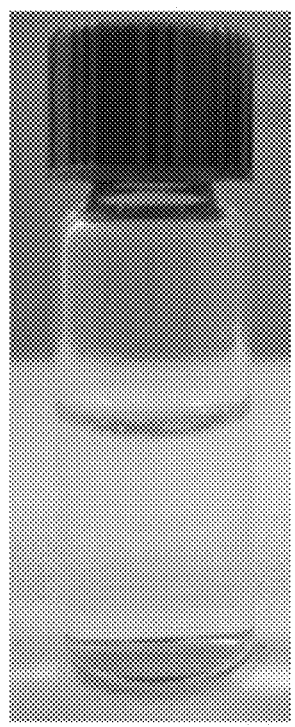 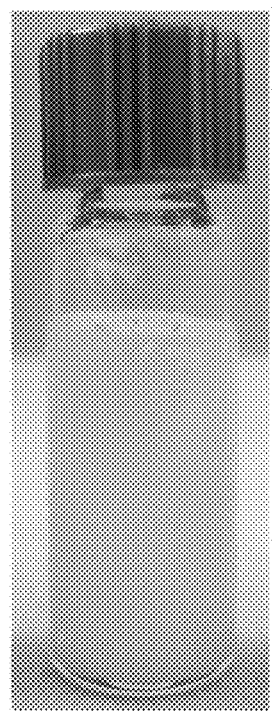
A. EESL + HESL    B. HESL
FIG. 25. MSL combinations.

MODIFIED SOPHOROLIPIDS AS OIL SOLUBILIZING AGENTS

STATEMENT OF RELATED APPLICATIONS

This patent application claims the benefit of and is a continuation-in-part of U.S. patent application Ser. No. 13/080,609 having a filing date of 5 Apr. 2011, which claims the benefit of and is a non-provisional of U.S. Provisional Patent Application 61/320,885 having a filing date of 5 Apr. 2010.

BACKGROUND OF THE INVENTION

Technical Field

The present invention relates generally to the field of sophorolipids (SL) and more specifically to new compositions of matter for uses of modified sophorolipids (MSL) and combination of sophorolipids as solubilizing agents, emulsifiers, dispersants and thereof.

Prior Art

Sophorolipids (SL) are glycolipid biosurfactant molecules produced by yeasts, such as *Candida bombicola, Yarrowi alipolytica, Candida apicola*, and *Candida bogoriensis*. Microbial biosurfactants are surface active compounds produced by various microorganisms. They lower surface and interfacial tension and form spherical micelles at and above their critical micelle concentration (CMC). Microbial biosurfactants generally have an amphiphilic structure, possessing a hydrophilic moiety, such as an amino acid, peptide, sugar or oligosaccharide, and a hydrophobic moiety including saturated or unsaturated lipid or fatty acids.

SLs consist of a hydrophilic carbohydrate head, sophorose, and a hydrophobic fatty acid tail with generally 16 or 18 carbon atoms with saturation or unsaturation. Sophorose is an unusual disaccharide that consists of two glucose molecules linked β-1,2. Furthermore, sophorose in SLs can be acetylated on the 6'- and/or 6"-positions (FIG. 1). One fatty acid hydroxylated at the terminal or subterminal (β-1) positions is β-glycosidically linked to the sophorose molecule. The fatty acid carboxylic acid group is either free (acidic or open form) or internally esterified generally at the 4"-position (lactonic form) (FIG. 1). The hydroxy fatty acid component of SLs generally has 16 or 18 carbon atoms with generally one unsaturated bond (Asmer et al. 1988; Davila et al. 1993). However, the SL hydroxy fatty acid can also be fully saturated, di-unsaturated or tri-unsaturated. As such, SLs synthesized by *C. bombicola* consist of a mixture of related molecules. Differences between these molecules are found based on: i) the fatty acid structure (degree of unsaturation, chain length, and position of hydroxylation), whether they are produced in the lactonic or ring-opened form, and ii) the acetylation pattern.

Studies have been carried out to "tailor" SL structure during in vivo formation. These studies have mainly involved the selective feeding of different lipophilic substrates. For example, changing the co-substrate from sunflower to canola oil resulted in a large increase (50% to 73%) in the lactonic portion of SLs (Tulloch et al. 1962; Asmer et al. 1988; Davila et al. 1992; Zhou et al. 1992, 1995). Also, unsaturated C-18 fatty acids of oleic acid may be transferred unchanged into SLs (Rau et al. 1999). Finally, lactonic and acidic SLs are synthesized in vivo from stearic acid with similar yields to oleic acid-derived SLs (Felse et al. 2007). Thus, to date, physiological variables during fermentations have provided routes to the variation of SL compositions.

As noted above, fermentation by different microorganisms, *Candida bombicola, Yarrowi alipolytica, Candida apicola*, and *Candida bogoriensis*, leads to sophorolipids of different structure noted above, the variations in sophorolipids based on fatty acid feedstocks and organisms leads to a wide array of sophorolipids including lactonic and acidic structures. An additional modification that is relevant to acidic sophorolipids is cleavage of the sophorose moiety to the corresponding glucose-based glucolipids. Treatment of acidic sophorolipids with enzymes β-glucuronidase (*Helix pomatia*), cellulase (*Penicillium funiculosum*), Clara diastase (a mixture of enzymes including amylase, cellulase, peptidase, phosphatase, and sulphatase), galactomannanase (*Aspergillus niger*), hemicellulase (*Aspergillus niger*), hesperidinase (*Aspergillus niger*), inulinase (*Aspergillus niger*), pectolyase (*Aspergillus japonicus*), or naringinase (*Penicillium decumbens*) afford glucolipids over a range of pH values (Rau et al. 1999) (for enzymatic treatment of SLs see FIG. Scheme 1).

In addition to tailoring SL in vivo formation, it is known that by chemical or enzymatic modification of SLs, their physical properties can be manipulated (Zhang et al., 2004). Modifications of SLs were performed so that the chain length of the n-alkyl group (methyl, ethyl, propyl, butyl, and hexyl) esterified to the SL fatty acid was varied. The effect of the n-alkyl ester chain length on interfacial properties of corresponding sophorolipid analogues was studied. The critical micelle concentration (CMC) and minimum surface tension have an inverse relationship with the alkyl ester chain length. That is, CMC decreased to ½ per additional $CH_2$ group for the methyl, ethyl, and propyl series of chain lengths. These results were confirmed by fluorescence spectroscopy. Adsorption of SL alkyl esters on hydrophilic solids was also studied to explore the type of lateral associations. These surfactants were found to absorb on alumina but much less on silica. This adsorption behavior on hydrophilic solids is similar to that of sugar-based nonionic surfactants and unlike that of nonionic ethoxylated surfactants. Hydrogen bonding is proposed to be the primary driving force for adsorption of the sophorolipids on alumina. Increase in the n-alkyl ester chain length of SLs caused a shift of the adsorption isotherms to lower concentrations. The magnitude of the shift corresponds to the change in CMC of these surfactants.

It has been shown that modified sophorolipids (MSLs) have antibacterial, antiviral, and anti-inflammatory properties (Mueller et al. 2006; Shah et al. 2005). In one example, MSLs were shown to down-regulate expression of pro-inflammatory cytokines including interleukin (Hagler et al. 2007). Furthermore, as shown in Table 1, the antibacterial activity of SLs can be increased by up to 1,000 times relative to the natural SL mixture by simple modifications such as esterification of fatty acid carboxyl groups and selective acetylation of disaccharide hydroxyl groups. Table 1 comprises a table of sophorolipid derivatives and sophorolipid components of the natural mixture used in bacterial and fungal plant pathogen assays. The hydroxylated fatty acid of the natural mixture is predominantly 17-hydroxyoleic acid. However, other fatty acid constituents with variations in chain length and unsaturation may also be present.

Our previous work on antimicrobial activity of MSLs showed antimicrobial activity against plant pathogens that include fungi, bacteria and their spores at 0.15 to 10 mg/mL minimum inhibitory concentrations (MIC) (U.S. patent application Ser. No. 12/360,486 and U.S. Provisional Patent Application No. 61/320,885). Further, formulation of MSLs with TWEEN® 20 brand of surface active agent and Polypropylene glycol increased the broad spectrum antimicrobial activity of SLs (U.S. Provisional Patent Application No. 61/543,122). While preparing MSL for formulation we noticed a surprising result, i.e., when we mix two or more modified SLs (e.g., compound 6 with 7), or modified sophorolipids with a natural sophorolipids, there is an increase in the solubility for the combined compounds in distilled water relative to these compounds individually. For example, a 1:1 mol/mol mixture of compound 6 and 7 in distilled water without any additives (e.g. TWEEN® 20 and Polypropylene glycol) was soluble up to 10 mg/L whereas the solubility of compounds 6 and 7 is less than 1 mg/L when they were studied separately/individually. Furthermore, when mixing modified SLs (e.g., compound 6 with 7), or modified sophorolipids with natural sophorolipids, there were extraordinary increases in mixture antimicrobial activity (U.S. patent application Ser. No. 13/757,762) relative to the antimicrobial activity for each of the components when presented individually. Moreover, we discovered that mixing modified SLs or a modified sophorolipids with a natural sophorolipids can result in enhanced performance properties for other applications. Furthermore, we also discovered that unexpected enhanced performance in specific applications may be discovered by exploring the properties of a modified sophorolipid library.

US Patent Publication. No. 2010/0098821 A1 discloses a process that solubilizes essential oils to produce clear beverages using ionic and non-ionic emulsifiers. The process described in this invention simplifies the introduction of normally insoluble nutraceuticals, particularly lipophilic ones, into beverages. Many ionic and non-ionic surfactants were described for use in formation of these emulsions such as sorbitan esters, polyglycerol esters, monoglyceride esters, diglyceride esters, polyethylene glycol esters, sucrose esters, dioctyl sodium sulfosuccinate and lecithin. Neither modified nor natural sophorolipids are mentioned in US Patent Publication. No. 2010/0098821 A1. Furthermore, because the composition of a flavor oil depends on its origin and processing, the most effective compounds for its solubilization cannot be anticipated by one skilled in the art. Hence, the availability of safe and effective compounds that prove useful for solubilization of various flavor and fragrance oil compositions are highly useful to formulators. This present disclosure provides methods for the formulation of micro- and nanoemulsions using one or mixtures of modified sophorolipids, mixtures of modified sophorolipids and natural sophorolipids, as well as mixtures containing one or move modified and/or natural sophorolipid with other molecules that are already known by one skilled in the art as being useful for solubilization of flavor and fragrance oils.

U.S. Pat. No. 6,214,957 B1 disclosed the use of solubilizers, emulsifiers and dispersing agents having the effects of moisturizing the skin when used as washing agents and having the character of elevating the concentration of a material to be solubilized, emulsified or dispersed in solvents including water as compared with the case where the material is employed alone, or elevating the apparent concentration of a material to be emulsified or dispersed in solvents by increasing homogeneity of the emulsion or dispersion which contain as the active ingredient polymers obtained by polymerizing monomer compositions containing at least one hydrophilic monomer (a i.e., 2-(methacryloyloxy)ethyl-2'-(alkyl-substituted or non-substituted ammonio)ethyl phosphate) having a group represented by general formula (1) in the side chain, wherein R1, R2 and R3 represent each H or C 1-4 alkyl group having 1 to 4 carbon atoms, and are the same or different groups) and, as a hydrophobic monomer (b), 0 to 80 weight % of (meth) acrylate. Furthermore, the solubilizers, emulsifiers and dispersing agents having the effects of moisturizing the skin described in U.S. Pat. No. 6,214,957 B1 have no or low bio-based content and are not fully biodegradable. In contrast, the present disclosure discloses MSLs with different chemical compositions that can be used in various combinations of other compounds, are highly effective molecules for a wide range of oil types such as fragrance, flavor and nutraceuticals compounds. Furthermore, modified sophorolipids are fully or highly bio-based and are completely biodegradable when disposed in many environments including in waste-water systems.

The present inventions suggest that by careful modulation of the SL structure via simple chemical modification methods, dramatic shifts in their interfacial activity can be achieved that allow them to be "tuned" or optimized so that highly effective MSL compounds are obtained for applications as solubilizing agents, emulsifiers, dispersants and thereof. The inventors are aware of no examples in prior patents or other literature sources that describe the method developed herein that comprises the development of a library of modified sophorolipids using a wide-range of chemical and enzyme catalyst tools to identify MSLs that can be used in pure form, as mixtures with other modified sophorolipids, as mixtures with natural sophorolipids, as mixtures with modified and natural sophorolipids, and as mixtures with other compounds known by one skilled in the art for use in the dispersion, solubilization or emulsification of various oil types and nutraceuticals.

The new solubilizing, emulsification and dispersant activities of MSLs and various combinations described above that are disclosed herein are unique in structure relative to known sophorolipid derivatives in previous art. It is to these needs and others that the present invention is directed.

BRIEF SUMMARY OF THE INVENTION

Briefly stated, the present invention is on application of MSLs either alone or in formulations with combinations of compounds that can consist of other MSLs, natural SLs and other known surface active compounds for use as solubilizing, emulsification, dispersing and surface active agents.

In the present disclosure, we disclose the unexpected results that MSLs, and mixtures thereof with natural and other modified sophorolipids, outperform natural SLs for solubilization or emulsification of various compounds such as crude oils, hydrocarbons, and food oils. The results disclosed herein are surprising and nonobvious given that there is no prior art disclosing that MSLs, mixtures of MSLs or mixtures of MSLs with natural sophorolipids could be beneficial to the property of solubilizing agents, emulsifiers, and dispersants activity. Furthermore, it is not obvious to one skilled in the art what modified sophorolipids will have preferred properties for the solubilization or emulsification of various oil phases.

MSLs and natural SLs that are useful in this invention and thereby incorporated herein are shown in FIGS. 1 to 11, FIGS. Scheme 1 and 2, and Table 1. For example, SLs that are useful in this invention include the following and their esters:

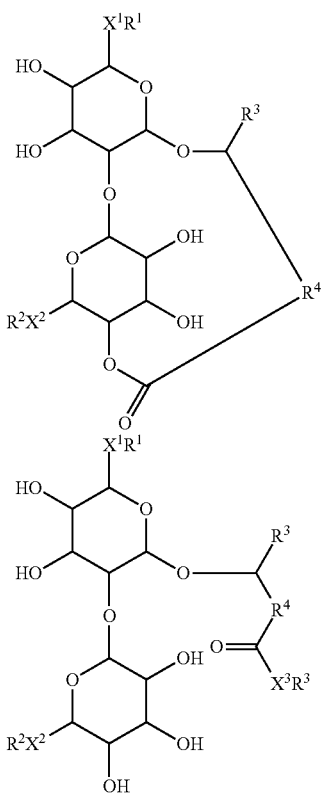

where $X^1=X^2=CH_2$.

In one embodiment:
- $X^1$ or $X^2$ is oxymethyl (—$CH_2O$—) or methylene (—$CH_2$—); and
- $R^1$ and/or $R^2$ are selected from the group of functional groups consisting of: hydrogen, acetyl, acryl, urethane, hydroxyalkyl, ether, halide, and carboxyalkyl or alkyl containing heteroatoms (1°, 2°, and 3° amino, tetraalkylammonium, sulfate, phosphate).

In another embodiment:
- $X^1$ or $X^2$ is carbonyl (—C=O—); and
- $R^1$ and/or $R^2$ are selected from the group consisting of: hydroxyl, amide, alkanamide, alkanamide containing heteroatoms (1°, 2°, and 3° amino, tetraalkylammonium), alkylsulfate, alkylphosphate, carbohydrate, and mono- or oligopeptide.
- $R^3$ is a hydrogen or alkyl group;
- $R^4$ is an alkyl chain that normally has 15 carbons but can have between 9 and 19 carbons and normally has unsaturation (C=C bond) at one or more sites. Derivatives in this invention include modifying unsaturated (C=C) bonds within $R^4$ to be saturated (by hydrogenation), epoxidized, hydroxylated (by hydrolysis of the epoxide or hydroboration oxidation or dihydroxylation using osmium tetroxide), or converted to a dithiirane, alkyl aziridine, cyclopropyl, thioalkane derivative. The methods involved in performing these chemical transformations are well known to those skilled in the art;
- $X^3$ contains heteroatoms (e.g., O, S, NH); and
- The combination of $X^3R^3$ is selected from the group of functional groups consisting of: hydroxy, alkanethiolate, amide, alkanamide, alkanamide containing heteroatoms (1°, 2°, and 3° amino, tetraalkylammonium), alkylsulfate, alkylphosphate, carbohydrate, and mono- or oligopeptide with 2-50 amino acids.

These features, and other features and advantages of the present invention will become more apparent to those of ordinary skill in the relevant art when the following detailed description of the preferred embodiments is read in conjunction with the appended tables, figures, and schemes.

BRIEF DESCRIPTION OF THE TABLES, SCHEMES, AND FIGURES

Table 1 comprises a table of Modified Sophorolipids (MSLs) and sophorolipid components of the natural mixture incorporated for use in this invention. The hydroxylated fatty acid of the natural mixture is predominantly 17-hydroxyoleic acid.

Table 2 comprises CMC values for SL-amides (from this invention) as well as SL-esters (from earlier publication in Colloids and surface 2004, 240, 75) for which surface activity but not interfacial activity was studied.

Table 3 comprises solubility results for SL-amides (compounds 22, 23, 24, and 25), SL-esters (compounds 6, 7, 8, and 16), unmodified natural SLs (compounds 1, 2, and 3) and SDS.

Table 4 comprises average droplet size determined by a Coulter LS 230 analyzer for paraffin oil-to-water (7:3 v/v) 24 hours after preparation stored at room temperature (25° C.).

Table 5 comprises average droplet size determined by a Coulter LS 230 analyzer for paraffin oil-to-water (7:3 v/v) emulsions aged for 3-months at room temperature (25° C.).

Table 6 comprises droplet size distribution of emulsions at different storage time for lemon oil solubilization by SL-hexyl ester (16), SL-octyl ester SL (17), SL-dodecyl ester (18), TWEEN® 60 and Rhamnolipid.

Table 7 comprises crude oil clearing/displacement activity of MSLs.

Table 8 comprises crude oil emulsification activity of MSLs.

FIG. Scheme 1 shows a summary of chemo-enzymatic chemistry developed to prepare a library of sophorolipid analogs (see Azim et al. 2006, Singh et al., 2003, Bisht et al, 2000, Bisht et al., 1999).

FIG. Scheme 2 shows a synthesis of diamide derivatives from lactonic sophorolipid using transalkylidenation followed by amidation reactions.

FIG. 1 shows the structure of lactonic and acidic forms of sophorolipid mixture produced by Candida bombicola.

FIG. 2 shows general formulas for sophorolipids and sophorolipid analogs of the present invention.

FIG. 3 shows natural sophorolipids in the lactonic form (Compound 2).

FIG. 4 shows sophorolipids in the open chain (acidic) form (Compound 3).

FIG. 5 shows representative ester derivatives of the open chain form.

FIGS. 6A-6B show amide and related derivatives of the open chain form, with FIG. 6B being a continuation of FIG. 6A.

FIG. 7 shows derivatives of the C=C (double bond) in the lactonic and open chain forms.

FIG. 8 shows modified sophorolipids in which the C=C (double bond) in the lactonic and open chain forms have been hydrogenated (hydrogenated natural SLs, Compound 4).

FIG. 9 shows peptide derivatives of the open chain form.

FIG. 10 shows trans alkylidenation derivatives of lactonic and open chain SLs.

FIG. 11 shows electrophile derivatives at sophorose ring.

FIG. 12 shows CMC of SL-amides, SL-esters and alkyl glucoside as a function of alkyl chain length.

FIG. 13 shows dilution test for O/W emulsions.

FIG. 14 shows emulsion with Compound 25 (SL-Hexyl Amide) at 2%, Oil/Water volume ratio=7/3 v/v.

FIG. 15 shows Emulsion phase separation for emulsions prepared using natural and modified sophorolipids$^a$ by homogenization of paraffin oil/water (5:5 volume ratio) and 2%-by-weight relative to the water phase.

FIG. 16 shows emulsion volume percentage change with time at oil/water=1/9 v/v.

FIG. 17 shows emulsion volume percentage change with time at oil/water=5/5 v/v.

FIG. 18 shows emulsion volume percentage change with time at oil/water=7/3 v/v.

FIG. 19 shows emulsion viscosity versus shear rate for oil/water=7/3 v/v and 2% SL-butyl ester (8) relative to paraffin oil.

FIG. 20 shows viscosity of emulsions prepared from paraffin oil/water 7:3 v/v stabilized by 1%-by-weight MSL or SDS as a function of aging time at room temperature (25° C.).

FIG. 21 shows viscosity of emulsions prepared from paraffin oil/water 7:3 v/v, aged for 24 hours at room temperature (25° C.), as a function of MSL or SDS concentration (weight-%-relative to the oil phase).

Figure 24:
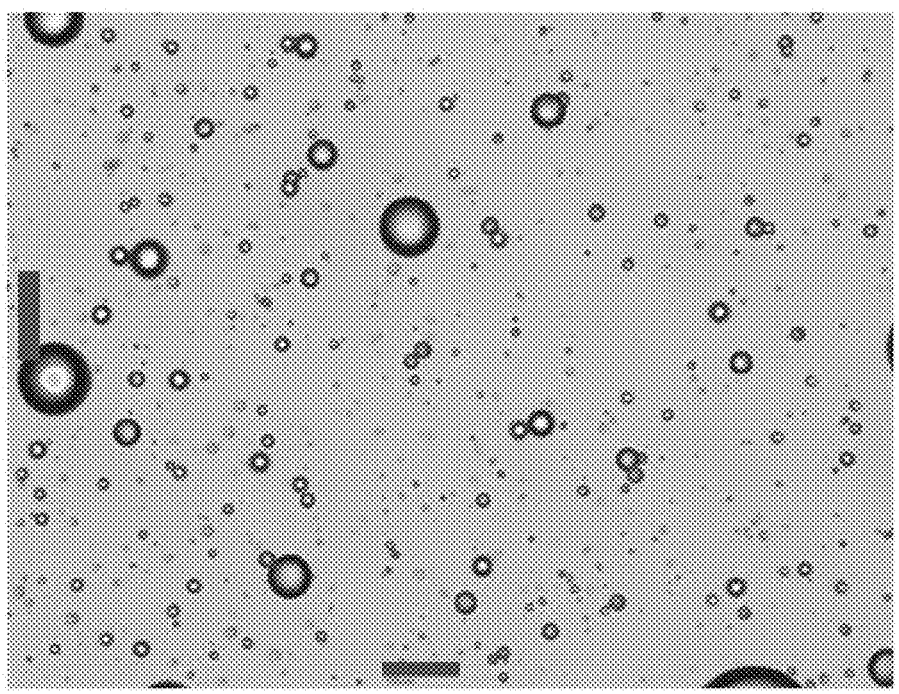

FIG. 22 shows 1 weight % surfactant, water:paraffin oil=1:1 v/v, the pictures were taken after 6 weeks using MSL compounds 39 and 43 (22a and 22b, respectively). During a 6-week aging period no substantial change in emulsions were observed. The cloudy parts are emulsified water, and the continuous phase is the oil.

FIG. 23A shows a microscopic image of sample A in FIG. 1 diluted in paraffin oil that contained sudan red. The image shows that a water-in-oil emulsion formed (scale bar: 100 μm). FIG. 23B shows a microscopic image of sample B in FIG. 23 diluted in paraffin oil. The water-in-oil emulsion was confirmed by dilution experiment, as dye experiment gave poor resolution (scale bar: 10 μm).

FIG. 24 shows a microscopic image of water-in-oil emulsion formed with rapeseeds oil using compound 40; picture was taken after 6 weeks and studies of the emulsion phase and emulsion droplet size shows the emulsion remained stable. Condition: 15% (v/v) of water in rapeseeds oil, 1 weight % (relative to water) of compound 40 were mixed and stirred using a homogenizer for 5 minutes (scale bar: 100 μm).

FIG. 25. MSL combinations. Emulsions were processed with a high shear homogenizer at 13,500 rpm. One example of this MSL combination formulation included 5 weight % surfactant, 1 weight % lemon oil, and 94% D.I. $H_2O$.

DETAILED DESCRIPTION OF PREFERRED EMBODIMENTS

In the present invention, solubilizing means obtaining a transparent or semitransparent homogenous solution when a substance to be solubilized is dissolved in a solvent. In the present invention, emulsifying means obtaining a homogenous emulsion when a substance to be emulsified is dispersed when a liquid substance and a solvent are emulsified. In the present invention, dispersing means obtaining a homogenous dispersion when a solid substance is dispersed in a solvent. The solubilizer, emulsifier or dispersing agent is an agent that improves solubility, emulsifying capacity or dispersion capacity of a solvent, compared to the inherent capacity of the solvent in which materials such as oils, cosmetics, pesticides, antimicrobials, hydrocarbons and drugs are dissolved, emulsified or dispersed alone. The present solubilizer, emulsifier or dispersing agent contains as an effective ingredient, MSL or ingredients, MSLs or combination of effective ingredients, MSLs with natural sophorolipids as solubilizers, emulsifiers, and dispersants.

MSLs and natural SLs that are useful in this invention and thereby incorporated herein are shown in FIGS. 1 to 11, FIGS. Scheme 1 and 2, and Table 1. In more detail:

FIG. 1 shows the structure of lactonic and acidic forms of sophorolipid mixture (Compound 1) produced by *Candida bombicola* (R=$COCH_3$ and/or H) used in the present invention.

FIG. 2 shows the general formulas for sophorolipids and sophorolipid analogs of the present invention.

FIG. 3 shows natural sophorolipids in the lactonic form (Compound 2), with $R^1$=H, Ac and $R^2$=H, Ac.

FIG. 4 shows natural sophorolipids in the open chain (acidic) form (Compound 3), with a mixture of $R^1$=$R^2$=Ac; $R^1$=Ac and $R^2$=H; $R^1$=H and $R^2$=Ac; and $R^1$=$R^2$=H.

FIG. 5 shows representative ester derivatives of the open chain form:

| Compound Code | R |
|---|---|
| 6 | $R^1 = R^2 = H; R^3 = Me$ |
| 7 | $R^1 = R^2 = H; R^3 = Et$ |
| 8 | $R^1 = R^2 = H; R^3 = Bu$ |
| 9 | $R^1 = Ac; R^2 = H; R^3 = Et$ |
| 10 | $R^1 = R^2 = Ac; R^3 = Et$ |
| 11 | $R^1 = H; R^2 = Ac; R^3 = Bu$ |
| 12 | $R^1 = R^2 = Ac; R^3 = Bu$ |
| 13 | $R^1 = H; R^2 = Ac; R^3 = Et$ |
| 14 | $R^1 = R^2 = H; R^3 = Propyl$ |
| 15 | $R^1 = R^2 = H; R^3 = Pentyl$ |
| 16 | $R^1 = H; R^2 = H; R^3 = Hexyl$ |
| 17 | $R^1 = H; R^2 = H; R^3 = Octyl$ |
| 18 | $R^1 = H; R^2 = H; R^3 = Dodecyl$ |

FIG. 6 shows amide and related derivatives of the open chain form:

| Compound Code | Sophorolipid amide derivatives - Compounds 19 to 31 |
|---|---|
| 19 | $R^3 = CH_2CH_2OH$ |
| 20 | $R^3 = CH_2CH_2NMe_2$ |
| 21 | $R^3 = CH_2CH_2NMe_3^+I^-$ |
| 22 | $R^3 = CH_3$ |
| 23 | $R^3 = CH_2CH_3$ |
| 24 | $R^3 = (CH_2)_3CH_3$ |
| 25 | $R^3 = (CH_2)_5CH_3$ |
| 26 | $R^3 = (CH_2)_7CH_3$ |
| 27 | $R^3 = CH_2CH_2SH$ |
| 28 | $R^3 = CH_2CH_2\text{-(1-pyrrolidinyl)}$ |
| 29 | $R^3 = CH_2CH_2\text{-(2-imidazolyl)}$ |
| 30 | saturated lipid moiety, $R^3 = CH_2CH_2NMe_2$ |
| 31 | saturated lipid moiety, $R^3 = CH_2CH_2NMe_3^+I^-$ |

| Compound Code | Sophorolipid biogenic amides - Compounds 32 to 38 |
|---|---|
| 32 | $(CH_2)_5NH_2$ |
| 33 | $R^3 = (CH_2)_4NH(CH_2)_3NH_2$ |
| 34 | $R^3 = (CH_2)_3NH(CH_2)_4NH\text{—}(CH_2)_3NH_2$ |
| 35 | $R^3 = CH_2CH_2\text{-(1-Imidazole)}$ |
| 36 | $R^3 = CH_2CH_2\text{-(m,p-benzenediol)}$ |
| 37 | $R^3 = CH_2CH_2\text{-(1-indole)}$ |
| 38 | $R^3 = CH_2CH_2\text{-(p-phenol)}$ |

FIG. 7 shows derivatives of the C=C (double bond) in the lactonic and open chain forms, with X=H, OH, $NH_2$, NHR, SH, SR, OR; Y=H, OH, $NH_2$, NHR, SH, SR, OR, and Z=O, NH, NR, S, CHR.

FIG. 8 shows modified sophorolipids in which the C=C (double bond) in the lactonic and open chain forms have been hydrogenated (hydrogenated natural SLs, Compound 4), with $R^1$=H, Ac; $R^2$=H, Ac.

FIG. 9 shows peptide derivatives of the open chain form.

FIG. 10 shows trans alkylidenation derivatives of lactonic and open chain SLs, with $R^3$=H, alkyl, aryl, heterocyclic, cationic, anionic groups. This is a first class of MSL derivatives that includes lactonic and acidic sophorolipids in which the C=C bond has been reduced by hydrogen in the presence of a catalyst.

FIG. 11 shows electrophile derivatives at sophorose ring, with E=$(CH_2-CH_2O)_nH$, $CH_2-CH(OH)-CH_2NMe_3^+$ or $H^+$. It is contemplated that the 6' and/or 6" positions of the sophorose ring may be alkylated by ethylene oxide or a substituted alkylene oxide such as 2,3-epoxypropyl-1,1,1-trimethylammonium chloride (Quab151) or related electrophiles.

Modifications of SLs from their natural form were described in our earlier US patent application, including U.S. patent application Ser. No. 12/360,486, having a filing date of 27 Jan. 2009; U.S. Provisional Patent Application No. 61/320,885, having a filing date of 5 Apr. 2010; U.S. Provisional Patent Application No. 61/543,122, having a filing date of 4 Oct. 2011; U.S. patent application Ser. No. 13/644,563, having a filing date of 4 Oct. 2012; and U.S. patent application Ser. No. 13/757,762, having a filing date of 4 Oct. 2012, and their chemical formula and structure are described in detail (compounds 1 to 35). In addition, this invention also discloses the synthesis of new MSL using cross metathesis chemistry (new compounds 36 to 41).

Embodiments of this invention include formulation of MSLs, natural SLs and their combinations with inert ingredients as listed in US Environmental Protection Agency's (EPA) eligible inert ingredients list (a current copy of which is attached hereto as Appendix 1, but which may be updated from time to time by the EPA) and any other material that could be used as an inert ingredient in the future. MSLs and combinations of MSLs described in this disclosure also include other MSL compositions that would be obvious to one skilled in the art based on review of this application or those encompassed within prior art.

Results And Discussion

Natural SLs and MSLs suitable for use in this invention include the following chemical compositions.

A first class of MSL derivatives includes lactonic and acidic sophorolipids in which the C=C bond has been reduced by hydrogen in the presence of a catalyst (FIG. 10). An exemplary reaction, applied to the conversion of lactonic sophorolipid (2) to hydrogenated lactonic sophorolipid (5), is shown below. It is contemplated that all of the derivatives (ester, amide, acetylated sophorose, inter alia) could be synthesized in a hydrogenated form. A related class of modifications at the C=C double bond include dihydroxylation carried out, for example, using the Sharpless asymmetric dihydroxylation catalyst. Other routes familiar to one skilled in the art would include acid catalyzed hydrolysis of the corresponding epoxide that could be generated using m-chloroperbenzoic acid or the Jacobsen epoxidation catalysts. A related class of modifications at the C=C double bond include the thiol-ene reaction that would lead to the formation of the corresponding thioether.

A second class of MSLs includes esterified ring-opened sophorolipids. Esterification of sophorolipids is achieved by alcoholysis of natural sophorolipid mixtures. Esters of varying chain lengths and with varying degrees of branching and containing a variety of heteroatoms are included in this invention (FIG. 5). Moreover, methods are already disclosed in the literature that describes selective acetylation of SLs at the 6'- and/or 6"-hydroxy sophorose groups. Therefore one skilled in the art will recognize that many variants may be generated by permutations of the ester functional group and sophorose acetyl groups.

A third class of sophorolipid derivatives includes amides of acidic sophorolipids. Representative examples of sophorolipid amide derivatives are shown in FIGS. 6A-6B. In the exemplary reaction shown, sophorolipid amides can be synthesized from the sophorolipid methyl ester derivative 6 by treatment with an amine at elevated temperature. It is contemplated that a variety of amines, diamines, triamines of differing chain lengths containing aliphatic, olefinic, acetylenic, and aromatic substituents can be used to synthesize the corresponding amide derivatives. Additionally, inclusive of this invention are amides derived from biogenic amines including, but not limited to, 4-aminosalicylic acid, 5-aminosalicylic acid, octopamine, 3-hydroxytyramine, phenethylamine, tryptamine, histamine, spermine, spermidine, 1,5-diaminopentane. Additionally, inclusive of this invention are amides bearing at the sophorose head group ionic moieties such as sulfate, sulfonate, phosphate, carboxylate and quarternary ammonium salts that result in cationic or anionic charged head groups. Additionally, it is contemplated that a variety of substituted amino-containing compounds can be used as a platform to expand the family of sophorolipid amides and that amino acids and polypeptides of varying chain lengths and composition can be incorporated (FIG. 9).

A fourth class of MSL includes ammonium salts derived from SL-amides with N',N'-dimethylamino moieties. An exemplary reaction is conversion of the sophorolipid N',N'-dimethylethylamide derivative into the corresponding ammonium salt by treatment with methyl iodide at elevated temperature. It is contemplated that the quaternary ammonium salt may be prepared from alkyl halides of varying chain length as well as β,β,β-diiodoalkanes, leading to the formation of a wide array of sophorolipid structures.

A fifth class of MSLs include those modified at the sophorose 6' or 6" positions by, inter alia, an activated acyl molecule such as the vinyl ester or alkyl ester of propionic acid catalyzed by an enzyme catalyst such as a lipase in conjunction with one or more of the modifications described herein. In one exemplary reaction (Bisht et al., 1999), the unsubstituted open-chain acidic sophorolipid is acetylated at the sophorose 6'-hydroxyl position. It is contemplated that carbonyl compounds of varying chain lengths and degrees of branching can be incorporated and that a variety of carbonyl-containing functional groups can be incorporated including succinate, malate and citrate. Additionally, it is contemplated that esters of amino acids and oligopeptides can be incorporated at the 6' and/or 6" positions of the sophorose ring. Finally, it is contemplated that the 6' and/or 6" positions of the sophorose ring may be alkylated (FIG. 11) by ethylene oxide or a substituted alkylene oxide such as 2,3-epoxypropyl-1,1,1-trimethylammonium chloride (Quab151) or related electrophiles as described by Solarek (1989). Such substitutions will likely occur at the primary (1°) 6' and/or 6" positions but may also occur at the secondary (2°) sophorose ring hydroxyl groups to generate mixtures of sophorolipid derivatives.

A sixth class of MSLs include those formed from transalkylidenation of carbon-carbon double bonds (C=C) within $R^4$ (FIG. 2) of lactonic or open-chain acidic sophorolipids (FIG. 1). Novel compounds in this class include alkenes with linear or branched alkyl substituents. Additional novel compounds contemplated in this class are those in which the olefinic carbon generated from a transalkylidenation of carbon-carbon double bonds (C=C) within $R^4$ is substituted with groups that contain an aryl, heterocyclic, cationic, anionic or neutral moieties (FIG. 10, $R^3$=H, alkyl, aryl, alkanamide, heterocycle). The transalkylidenation chemistries described herein can be applied to carbon-carbon double bonds (C=C) within $R^4$ for both the open chain and lactonic SL forms (see FIG. 2). Furthermore, combinations of metathesis (performed on either the lactonic or open chain SL) and chemical modification can be anticipated. As one illustrative example, the cross metathesis of lactonic sophorolipid with vinyl acrylate will produce a diester wherein each of the ester groups can be converted into the corresponding amide derivative (FIG. Scheme 2).

A seventh class of MSLs includes MSLs synthesized using cross metathesis chemistry as described here. For the synthesis of compounds 39 to 44, lactonic sophorolipids were dissolved in THF (0.54M) at 60° C., and then 4 mol equivalent of acrylates (with various ester chain lengths) were added along with 5 mol % M2 catalysts (1,3-bis(2,4,6-trimethylphenyl)-2-imidazolidinylidene]dichloro-(3-phenyl-1H-inden-1-ylidene) (tricyclohexylphosphine)ruthenium(II)). The reaction was quenched by adding ethyl vinyl ether. The conversion was higher than 90%. The products were recrystallized in ethyl acetate and hexane. For compound 44, compound 37 was added in ethanol sodium ethoxide solution. The reaction mixture was refluxed for 3 hours, and neutralized before the solvent was removed. The crude product was then separated with chloroform and water; the product was recovered from the aqueous phase.

Representative Examples of critical micelle concentrations (CMC) and solubilizing, emulsification and dispersing Natural SLs and MSLs Example 1. CMOs of MSL Esters and Amides The surface tension change with the increase of surfactant concentration of a series of SL amides was measured at 25° C. and the results are shown in Table 2. CMC and minimum surface tension (MST) decrease as the chain length of the n-alkyl amide moiety increase. The same trend was observed for both series that CMC and MST decrease with the increase of alkyl chain length. This trend can be explained by the increased hydrophobicity of the surfactant hydrophobic tail with increased chain length of the n-alkyl amide.

The relation of CMC within a homologous series of surfactants and the carbon chain length (straight-chain), n, is usually described as:

$$\text{Log (CMC)} = A - Bn \quad (1)$$

Where A and B are constants specific to the series and n is the carbon on the hydrophobic chains. It was reported that the CMC of alkyl-β-D-glucoside decreased by ⅓ for each additional $CH_2$ group (L. Zhang. D.E.S. Thesis, Columbia University). For a series of SL-esters prepared from n-alkanols of varying chain length, the CMC decreased by ½ per additional $CH_2$ group (L. Zhang Colloid Surface, 240, 2004, 75). The results reported herein show that the CMC of methyl, ethyl, butyl and hexyl SL-amides decreased by around ⅗ per additional $CH_2$ group (FIG. 12). FIG. 12 shows CMC of SL-amides, SL-esters and alkyl glucoside as a function of alkyl chain length.

Surprisingly, the SL-amide series has higher (5 to 8 times) CMC and higher MST than the corresponding SL-ester series. It appears that compared to the ester bond, the amide bond is more disruptive to organization of the corresponding MSL's. One skilled in the art could not have anticipated that the SL-amide n-alkyl series would have higher (5 to 8 times) CMC and higher MST than the corresponding SL-ester series. Amides could have provided better stabilization of micelles through strong hydrogen bonding interactions. Instead the esters pack more easily into micelles at relatively low concentration and have a lower MST than the corresponding amide analogues.

Example 2. Emulsification Activity of MSLs with Paraffin Oil

Emulsion Type

Dilution Test:

In this test the emulsion is diluted either with oil (O) or water (W). If the emulsion is O/W type and it is diluted with water, it will remain stable as water is the dispersion medium. However, if the emulsion is O/W type and it is diluted with oil, the emulsion will break as oil and water are not miscible with each other. Oil-in-water emulsions can easily be diluted with an aqueous solvent whereas water-in-oil emulsions can be diluted with an oily liquid. Emulsions of the O/W type have separated layers after dilution with pure oil but form a homogenous phase when diluted by water. Unless otherwise specified, the emulsion type formed by MSLs were oil in water.

FIG. 13 shows dilution tests for O/W type emulsions. FIG. 13A displays two replicate test tubes with an O/W emulsion (1 mL total volume with water/oil ratio 5/5) stabilized by 2 weight % SL-hexyl amide (Compound 25, Table 1) where the oil phase was paraffin. In FIG. 13B, the tube on the left was diluted with 1 mL of oil whereas the tube on right was diluted with water. Visual observation of the tubes in FIG. 13B supports that the emulsions formed are indeed O/W emulsions.

Characterization of Emulsion with Water and Oil Soluble Dye Staining

Oil Red O was applied as an oil soluble dye and emerald green as water soluble dye in the process of emulsion preparation. Observations of emulsions were made before and after staining under optical microscope at 400× magnification (FIG. 14). FIG. 14 shows emulsion with Compound 25 (SL-Hexyl Amide) at 2%, Oil/Water volume ratio=7/3. FIG. 14A shows emulsion before dye stained and FIG. 14B shows emulsion after dye stained by Oil Red O. From the microscopic observation, staining of the droplet center red by the oil soluble dye Oil Red O indicates the emulsion type is O/W (see FIG. 14B). This result was obtained when studying MSL-ester compounds 6, 7, 8 and 16 as well as MSL-amide compounds 22, 23, 24 and 25, Table 1) as emulsifiers at 2%-by-weight relative to the water phase and oil/water volume ratios of 5/5 and 7/3. The formation of O/W emulsions and not W/O emulsions with this set of MSL compounds would not be obvious to one skilled in the art. We believe that O/W emulsions are formed by this set of MSLs due to that large sophorose polar head groups requires relatively more space than the lipid tails and, therefore self-assemble into spherical type structures where disaccharide groups are locating outside the droplets.

Solubility of MSLs in Water

Eight MSLs that include four SL-amides (compounds 22, 23, 24 and 25, Table 1) and four SL-esters (compounds 6, 7, 8 and 16) along with three non-modified SLs (compounds 1, 2 and 3) were studied to evaluate their water solubility. Solubility tests were conducted by adding 20 mg of the MSL or SDS to distilled water, heating while vortexing for 2 minutes and then maintaining the temperature at 25° C. without agitation for 10 minutes. If the material precipitates upon cooling or was to some extent insoluble, the insoluble material was separated by filtration, dried and weighed. Hence, the solubility of compounds was then determined by subtracting the insoluble material from the 20 mg added initially to [X mL] distilled water. Table 3 lists the solubility of these compounds. Direct comparison of SL-amides and SL-esters having identical alkyl amide and alkyl ester chain lengths showed the amides have much greater solubility. The greatest difference was for the methyl amide and methyl ester MSLs which have solubilities of >60 and <1 mg/mL, respectively. The acidic SL showed good solubility (>50 mg/mL) whereas the solubility of lactonic SL was <5 mg/mL. Correspondingly, SDS had the highest solubility (>100 mg/mL). It is reasonable to assume that the insoluble fraction of compounds can still participate in the process of emulsion formation by residing at the oil-water interface.

Emulsion Stability Based on Phase Separation

The paraffin oil/water volume ratio was 5/5 and the emulsifier content was 2%-by-weight relative to the water phase. The emulsion was obtained by homogenizing the oil and water mixture and was allowed to settle at room temperature for 24 hours. Thereafter, the volumes of the different phases in the emulsion (oil/emulsion/water) were measured (FIG. 15, which shows the results after 24 hours). FIG. 15 shows emulsion phase separation for emulsions prepared using natural and modified sophorolipids by homogenization of paraffin oil/water (5:5 volume ratio) and 2%-by-weight relative to the water phase.

a) MA: SL-Methyl Amide (22); EA: SL-Ethyl Amide (23); BA: SL-Butyl Amide (24); HA: SL-Hexyl Amide (25); ME: SL-Methyl Ester (6); EE: SL-Ethyl Ester (7); BE: SL-Butyl Ester (8); HE: SL-Hexyl Ester (16); AC: Acidic SL (3); LA: Lactonic SL (2); NA: Natural SL (1); SDS: Sodium dodecyl sulfate.

b) Emulsions were prepared by adding 5 mL of paraffin oil into 5 mL of water containing 2%-by-weight of the emulsifier. Then, this mixture was homogenized at 13,000 rpm for 2 minutes. Thereafter, the resulting emulsion was left unagitated at 25° C. for 24 hours.

Surfactants which give a larger emulsion phase are denoted as having higher emulsion effectiveness (Process Safety and Environment protection, 2005, 83, 38-46). For the eight modified SL derivatives that include four SL-amides (compounds 22, 23, 24 and 25, Table 1) and four SL-esters (compounds 6, 7, 8 and 16) along with three non-modified SLs (compounds 1, 2 and 3), the emulsion layer increased with increase of the alkyl chain length. For example, after 24 hours, no emulsion layer was observed for SL-methyl amide, SL-ethyl amide (compounds 22 and 23, respectively), and SL-methyl ester (compounds 6 and 7, respectively), however, the emulsion layer percentages for SL-butyl amide (24), hexyl amide (25), butyl ester (8) and hexyl ester (16) were 20%, 60%, 55% and 65%, respectively. Thus, unexpectedly, that longer alkyl chains, at least up to butyl and hexyl, provided improved interfacial stability at the paraffin oil/water interface. Moreover, SL-esters having identical alkyl chain length as their corresponding amide derivative were more effective emulsifiers. Apparently, ester bonds of SL-esters are less disruptive to organization at the oil water interface than amide bonds of SL-amides. For unmodified SLs, the lactonic SL (2) was not effective in emulsification of paraffin oil under the conditions studied herein. This result could not have been anticipated by one skilled in the art. The acidic SL (3) gave an 8% emulsion layer, much lower than the MSL examples given herein. Similarly, the natural SL (1) mixture gave a 10% emulsion layer. This performance is also far below that of SL-butyl amide (24), hexyl amide (25), butyl ester (8) and hexyl ester (16). Of the MSLs studied in this example, SL-hexyl ester (16) has the highest emulsion effectiveness and showed similar effectiveness to SDS (70% emulsion).

Emulsion Stability with Different Oil/Water Ratio.

Based on the effectiveness study, SL-butyl amide (24), hexyl amide (25), butyl ester (8), hexyl ester (16), and SDS as a reference commercial emulsifier were tested as emulsifying compounds for paraffin oil/water emulsions prepared by homogenization having different oil/water ratios. The concentration of MSLs and SDS was kept constant at 2%-by-weight relative to the water phase and the oil/water volume ratios evaluated were 1/9, 5/5 and 7/3. After homogenized at 13,000 rpm for 2 minutes, the emulsions were kept at room temperature and separation of the respective oil, emulsion and water layers was recorded for up to 1 month. The stability of the emulsion phase was plotted as a function of time and the results are shown in FIGS. 16, 17 and 18. FIG. 16 shows emulsion volume percentage change with time at oil/water=1/9 v/v. FIG. 17 shows emulsion volume percentage change with time at oil/water=5/5 v/v. FIG. 18 shows emulsion volume percentage change with time at oil/water=7/3 v/v.

At the paraffin oil/water volume ratios tested that included 1/9, 5/5 and 7/3, SL-esters were discovered to provide higher stabilization of the emulsification phase as a function of time than corresponding SL-amides with the same alkyl chain length. Furthermore, this invention discloses that SL-butyl ester has a better ability to stabilize the emulsion phase than SL-hexyl amide over a wide range of paraffin oil-to-water volume compositions. For example, at oil/water 5/5 (FIG. 17), using SL-butyl amide, the emulsion layer of was not observed in 3 days. However, using SL-butyl ester, the emulsion layer showed a small decrease in volume-% (65 to 50%) in one month. Also, at oil/water 5/5, using SL-hexyl amide, the emulsion layer decreased from 65% to 10% in one month. Surprisingly, using the SL-hexyl ester at oil/water 5/5, the emulsion layer showed only a small decrease in volume-% (70 to 65%) in one month.

In FIG. 18, emulsion formation and stability results for paraffin oil/water volume ratios of 7/3 are displayed. Surprisingly, SL-butyl ester and hexyl ester formed a 95% emulsion layer, which is higher than that formed using SDS as the emulsion stabilizer (90%). The emulsion phases formed at this oil-to-water ratio show excellent stability. For example, by using SL-butyl ester and SL-hexyl ester as emulsion stabilizers, the emulsion phase decreased from 95% to 90 and 85%, respectively, over the one month aging period.

Emulsion Droplet Size Distribution Measurement

Table 4 shows the average droplet size of diluted emulsions after 24 hours of preparation as a function of emulsifier concentration and MSL structure.

Emulsified oil droplet size (average and standard deviation) was measured after suitable dilution of the emulsion phase using a Coulter LS 230 analyzer. While the particle sizes of emulsions showed no substantial change by increasing the surfactant concentration from 0.5 to 1.0%, further increase in the surfactant concentration to 2% did result in significantly smaller emulsion drop sizes. Furthermore, for the same concentration of surfactant, emulsion oil-phase drop sizes showed no significant change for the surfactants studied in Table 4. Therefore, surprisingly, similar size emulsion phase droplets were formed for MSL's in Table 4 and SDS. Relative to natural and lactonic SL, selected MSLs show improved properties as emulsifiers on paraffin oil. These data support our development of effective MSL emulsifiers that are largely bio-based and are biodegradable in bioactive disposal systems such as waste-water treatment plants.

After being aged for 3-months, emulsified oil droplet size (average and standard deviation) was measured after suitable dilution of the emulsion phase using a Coulter LS 230 analyzer and the results are listed in Table 5. Similar to results for emulsions aged for 24 hours, emulsion phase droplet size after 3-months aging showed no substantial change as the surfactant concentration increased from 0.5 to 1.0%-by-weight with the possible exception of SL-butyl amide. However, increasing the surfactant concentration from 1 to 2% did result in substantially smaller emulsion-phase droplet sizes. Furthermore, comparing Tables 4 and 5 shows that at 1% and 2% surfactant droplet sizes are similar for 24 hours and 3 month aging. This is evidence that MSL's can stabilize oil phases greatly decreasing their tendency to undergo coalescence. Based on Table 5, stabilization against coalescence by selected MSLs, in this case SL-butyl ester and SL-hexyl ester, is on par with that attained using the commercial product SDS. It follows that the results of 3-month aging studies support the utility of selected MSLs for formation and stabilization of oil-in-water emulsions of paraffin oil phases. One skilled in the art would expect that the ability of these MSLs to stabilize paraffin oil phases teaches that they would also stabilize oil phases of similar structure.

Emulsion Viscosity Measurement

Viscosity was measured at 25° C. with increasing shear rate from 1 $S^{-1}$ to 750 $S^{-1}$. The viscosity change was monitored for aging times up to 3 months. For all samples, the paraffin oil/water ratio is 7/3 and the surfactant concentrations studied were 0.5%, 1% to 2%-by-weight relative to the oil phase. FIG. 19 presents the viscosity change with shear rate for different aging times. FIG. 19 shows emulsion viscosity versus shear rate for oil/water=7/3 v/v and 2%-by-weight SL-butyl ester (8) relative to paraffin oil. The emulsion tested was prepared using 2%-by-weight SL-butyl ester relative to paraffin oil. Viscosity decreases with increased shear rate implying the emulsion follows shear shinning. Furthermore, viscosity decreased with increased storage time. For example, after 3 months, the viscosity at shear rate $1S^{-1}$ decreased by 19.1%, from 465 Pas to 376 Pas. This change is consistent with the small increase in oil phase particle size (1.7 to 2.1 µm) with aging from 1 day to 3-months (Tables 4 and 5).

FIG. 20 shows plots of emulsion viscosity at low shear viscosity ($\eta_{low}$, viscosity measured at shear rate $1^{-S}$) for emulsions prepared using 1% MSL and paraffin oil/water 7/3. FIG. 20 shows viscosity of emulsions prepared from paraffin oil/water 7:3 stabilized by 1%-by-weight MSL or SDS as a function of aging time at room temperature (25° C.). Values of $\eta_{low}$ decreased with storage time to various extents that are dependent on the MSL compound used to stabilize the emulsion. The extent of viscosity decrease (from lowest to highest) with storage time was in the following order: SL-hexyl ester<SDS<SL-butyl ester<SL-hexyl amide<SL-butyl amide. The relative ability of different MSL structures to stabilize emulsions and thereby decrease the extent of decrease in viscosity as a function of aging time would not be predictable by one skilled in the art. The behavior as a function of MSL structure is related to emulsion dispersed phase droplet size. That is, the smaller the change in droplet size, the less decrease in emulsion viscosity occurs with increased aging time. Smaller changes in droplet size reflects the ability of the emulsifier to better stabilize particles. For example, the viscosity of the emulsion stabilized by SL-butyl amide decreased by 65% (from 344 Pas to 120 Pas) whereas the viscosity of the emulsion stabilized by SL-hexyl ester decreased by 20% (from 457 Pas to 459 Pas). This result is consistent with the relatively better ability of SL-hexyl ester to retain a small droplet size compared to SL-butyl amide over the aging period. Furthermore, SL-hexyl ester shows almost identical properties in emulsion stability as SDS. Given the commercial importance of SDS, this shows the utility of the invention described here.

The relationship between emulsion viscosity and surfactant concentration is displayed in FIG. 21. FIG. 21 shows viscosity of emulsions prepared from paraffin oil/water 7:3, aged for 24 hours at room temperature (25° C.), as a function of MSL or SDS concentration (weight-%-relative to the oil phase). The viscosity was measured 24 hours after emulsion preparation. The viscosity increased with increasing surfactant concentration. Such behavior could not have been predicted by one skilled in the art without the teaching provided in this disclosure. The extent of viscosity change with surfactant concentration is related to the interfacial free energy at the droplet surface that reduces with the increase of surfactant concentration.

Example 3. Oil Solubilization Activity of MSLs on Lemon and Orange Oils

The oil solubilization of lemon oil by MSL's was demonstrated through experiments and observations. MSL's used in this example are SL-hexyl ester (16), SL-octyl ester SL (17), and SL-dodecyl ester (18). To test the MSL capacity for lemon oil solubilization, the volume ratio of water to lemon oil, the concentration of surfactant, and the homogenization time (using a sonicator as the means of homogenization) were varied. Concentration of surfactant is calculated on a w/w basis relative to the mass of water being used. To form emulsions, the MSL or other surfactant is first dissolved in the water, oil is added to the solution, and finally the contents of the water/surfactant+oil system is sonicated. Subsequently, the emulsion is allowed to settle for 24 hours at 25° C. before measurements or visual observations are made.

To evaluate the stability of lemon oil solubilization, photographs of emulsions were recorded daily (after the initial 24 hours). Visual observations consisted of assessing solution clarity, extent of creaming and whether oil separation occurs. After selected time periods measurement of emulsion droplet size was performed by dynamic light scattering, which gives an average droplet size in the solution. Droplet size results in Table 6 show that, after one month, all three MSLs (SL-hexyl ester (16), SL-octyl ester SL (17), and SL-dodecyl ester (18)) have average droplet sizes well below 1 µm. If the emulsion had creamed (separated into two discreet emulsion layers) the average droplet size for each emulsion layer was determined. The results of this study are listed in Table 6, where the first number represents average droplet size in the top emulsion layer and the second represents the average droplet size in the bottom emulsion layer. The presence of emulsion droplets in solution, along with visual observations from photographs, show that the lemon oil remains solubilized after aging at room temperature (25° C.) for one month. A better performing emulsifier for this study is defined as functioning to form emulsions with smaller average particle size after the aging period. Results in Table 6 shows that SL-hexyl ester (16) outperforms TWEEN® 60 and Rhamnolipid, two comparable and commonly used emulsifying compounds, after a one month aging period.

By using 1% SL-hexyl ester to form and stabilize emulsions with a lemon oil/water volume ratio of 1/99, the average size of dispersed oil phase droplets was 22 and 52 nm for aging times of one week and 1 month, respectively. For emulsions formed by SL-octyl ester (17) and SL-dodecyl ester (18), under the identical conditions used for SL-hexyl ester for a lemon oil/water volume ratio of 1/99, larger average sizes of the lemon oil dispersed phase were observed (see Table 6). The differences in performance of MSL esters as a function of alkyl ester chain length taught in this disclosure were unexpected and could not have been predicted by one skilled in the art.

In addition to testing single MSL emulsification through tracking nanoemulsion stability, MSL combinations were investigated. These emulsions were processed with a high shear homogenizer at 13,500 rpm. One example of this MSL combination formulation included 5 weight % surfactant, 1 weight % lemon oil, and 94% deionized water. The pure form of this formulation included 5 weight % SL-hexyl ester. The combination form of this formulation included 2.5 weight % SL-hexyl ester and 2.5 weight % SL-ethyl ester. The SL-hexyl ester emulsion, after having been kept at 25° C. for one week, was completely opaque, showed surfactant precipitation and possible gelling. The size of droplets within this emulsion was 2.5 μm. The combination emulsion was, after having been kept at 25° C. for one week, was crystal clear (comparable to water) with no surfactant precipitation. The size of droplets within the combination emulsion was 8.4 nm. FIG. 25 shows representative results of this testing. FIG. 25 shows MSL combinations in which FIG. 25A is 5 weight % EESL+HESL, 1 weight % Lemon Oil; and FIG. 25B is 5 wt % HESL, 1 wt % Lemon Oil.

Example 4. Oil Clearing/Displacement Activity of MSLs with Crude Oils

Oil cleaning assays were performed using Louisiana Crude, Arabian Light Crude, and Prudhoe Bay Crude as the oil phase. In one study, the oil clearing/displacement activity of MSLs were assessed using a crude oil layer on top of sea water in order to simulate oil spill type conditions. Sea water (20 mL) was transferred to plastic Petri dishes and 20 μL of a crude oil type was added on top of the water to create an oil layer. Subsequently, a 20 μL aliquot of MSL solution (1 mg/mL) was added dropwise to the top of the oil layer. The instantaneous formation of an oil clearing zone as well as the diameter of the clearing zone was determined as a function of the dispersant used. Surprisingly, when the dispersant was either SL-methyl ester, SL-ethyl ester or SL-butyl ester, the instantaneous formation of a clearing zone was observed for all of the crude oils studied. The oil displacement activity measured (diameter of the clearing zones) are listed in Table 7. Commercial surfactants Triton-X 100 and SDS were also assessed for their oil dispersion activity and a negative control was maintained with distilled water (with no added MSLs). Higher Louisiana crude oil displacement activities were seen for SL-methyl ester, SL-ethyl ester and SL-butyl ester relative to Triton X-100. Furthermore, the oil displacement activity of SL-ethyl ester and SL-butyl ester was slightly higher than Triton-X-100 for Arabian Light crude. In addition, all three of these MSLs had much higher oil displacement activity than SDS for the three crude oils tested. The high activity of MSLs for oil displacement could not have been anticipated by one skilled in the art and demonstrates the general utility sophorolipid alkyl esters for this application.

Example 5. Emulsification Activity of MSLs with Crude Oils

Emulsification activity was assessed using Louisiana Crude, Arabian Light Crude, and Prudhoe Bay Crude as the oil phase. A 2 mL solution with emulsifier concentration of 1 mg/mL was prepared. A crude oil (10 mg) was added to the emulsifier aqueous solution, the mixture was vortexed for one minute and the emulsified mixture was allowed to stand for 20 minutes. Emulsification activity was determined by measuring turbidity of the emulsion mixture in a spectrophotometer at 610 nm. The results obtained using SL-ethyl ester, SL-butyl ester, the natural sophorolipid mixture and Triton X-100 as emulsifiers are expressed as $D_{610}$ and are listed in Table 8. Surprisingly, the highest emulsification activity for all of the surfactants and oil phases tested was obtained by using SL-butyl ester as emulsifier. Furthermore, a remarkable improvement in emulsification activity was obtained for SL-butyl ester relative to the natural sophorolipid mixture. These comparative results for emulsification of Louisiana Crude, Arabian Light Crude, and Prudhoe Bay Crude oil phase could not be anticipated by one skilled in the art.

Example 6. Emulsification Activity of Paraffin Oil and Rapeseed Oil Using a Family of Ma's Prepared by Transalkylidenation of Lactonic SL C═C Bonds with Various n-Alkyl Acrylates Mixtures of oil (paraffin or rapeseed) and water, in a 1:1 volume ratio, were prepared. MSL compounds 39, 40, and 41 at 1 weight % relative to water were each assessed as emulsifiers. Each mixture was agitated for 5 min using a homogenizer. Results obtained in this study revealed these MSL derivatives formed water-in-oil emulsions and the emulsions were stable during the 6-weeks they were monitored (FIGS. 22 and 23). This is in contrast to the studies above where sophorolipid esters and amides consisting of one hydrophobic arm formed oil-in-water mixtures. For compound 43 that has relatively more hydrophobic character than MSL compounds 39. 40 and 41, paraffin oil and water (1:1 volume ratio) were combined and MSL compound 43 (2 weight % to water) was then added. The mixture was agitated by a homogenizer for 5 minutes. Results from this study with compound 43 revealed that the oil phase was completely emulsified forming a water-in-oil emulsion. The emulsion was stable during the 3 weeks it was monitored (FIG. 24). FIG. 22 shows 1 weight % surfactant, water: paraffin oil=1:1 (v/v), the pictures were taken after 6 weeks using MSL compounds 39 and 43 (22a and 22b, respectively). During a 6-week aging period no substantial change in emulsions were observed. The cloudy parts are emulsified water, and the continuous phase is the oil. FIG. 23A shows a microscopic image of sample A in FIG. 1 diluted in paraffin oil that contained sudan red. The image shows that a water-in-oil emulsion formed (scale bar: 100 μm). FIG. 23B shows a microscopic image of sample B in FIG. 23 diluted in paraffin oil. The water-in-oil emulsion was confirmed by dilution experiment, as dye experiment gave poor resolution (scale bar: 10 μm). FIG. 24 shows a microscopic image of water-in-oil emulsion formed with rapeseeds oil using compound 40; picture was taken after 6 weeks and studies of the emulsion phase and emulsion droplet size shows the emulsion remained stable. Condition: 15% (v/v) of water in rapeseeds oil, 1 weight % (relative to water) of compound 40 were mixed and stirred using a homogenizer for 5 minutes (scale bar: 100 μm).

The foregoing detailed description of the preferred embodiments and the appended tables, schemes, and figures have been presented only for illustrative and descriptive purposes and are not intended to be exhaustive or to limit the scope and spirit of the invention. The embodiments were selected and described to best explain the principles of the invention and its practical applications. One of ordinary skill in the art will recognize that many variations can be made to the invention disclosed in this specification without departing from the scope and spirit of the invention.

TABLE 1

Modified Sophorolipids (MSLs) and sophorolipid components of the natural mixture incorporated for use in this invention. The hydroxylated fatty acid of the natural mixture is predominantly 17-hydroxyoleic acid.

| Class/Structure | Substituent(s) | Code |
|---|---|---|
| Natural Sophorolipids | Mixture of 2 and 3 | 1 |
| Lactonic Sophorolipids (mixture) | $R^1 = R^2 = OAc$<br>$R^1 = H; R^2 = OAc$<br>$R^1 = OAc; R^2 = H$<br>$R^1 = R^2 = H$ | 2 |
| Acidic Sophorolipids (mixture) | $R^1 = R^2 = OAc$<br>$R^1 = H; R^2 = OAc$<br>$R^1 = OAc; R^2 = H$<br>$R^1 = R^2 = H$ | 3 |
| Hydrogenated natural sophorolipids | Mixture | 4 |
| Hydrogenated lactonic sophorolipids | $R^1 = R^2 = Ac$ | 5 |
| Sophorolipid Esters | $R^1 = R^2 = H; R^3 = Me$ | 6 |
| | $R^1 = R^2 = H; R^3 = Et$ | 7 |
| | $R^1 = R^2 = H; R^3 = Bu$ | 8 |
| | $R^1 = Ac; R^2 = H; R^3 = Et$ | 9 |
| | $R^1 = R^2 = Ac; R^3 = Et$ | 10 |
| | $R^1 = H; R^2 = Ac; R^3 = Bu$ | 11 |
| | $R^1 = R^2 = Ac; R^3 = Bu$ | 12 |
| | $R^1 = H; R^2 = Ac; R^3 = Et$ | 13 |
| | $R^1 = R^2 = H; R^3 = propyl$ | 14 |
| | $R^1 = R^2 = H; R^3 = pentyl$ | 15 |
| | $R^1 = R^2 = H; R^3 = Hexyl$ | 16 |
| | $R^1 = R^2 = H; R^3 = Octyl$ | 17 |
| | $R^1 = R^2 = H; R^3 = Dodecyl$ | 18 |

TABLE 1-continued

Modified Sophorolipids (MSLs) and sophorolipid components of the natural mixture incorporated for use in this invention. The hydroxylated fatty acid of the natural mixture is predominantly 17-hydroxyoleic acid.

| Class/Structure | Substituent(s) | Code |
|---|---|---|
| Sophorolipid Amides | $R^3 = CH_2CH_2OH$ | 19 |
| | $R^3 = CH_2CH_2NMe_2$ | 20 |
| | $R^3 = CH_2CH_2NMe_3^+$ | 21 |
| | $R^3 = CH_3$ | 22 |
| | $R^3 = CH_2CH_3$ | 23 |
| | $R^3 = (CH_2)_3CH_3$ | 24 |
| | $R^3 = (CH_2)_5CH_3$ | 25 |
| | $R^3 = (CH_2)_7CH_3$ | 26 |
| | $R^3 = CH_2CH_2SH$ | 27 |
| | $R^3 = CH_2CH_2$-(1-pyrrolidinyl) | 28 |
| | $R^3 = CH_2CH_2$-(2-imidazolyl) | 29 |
| Hydrogenated sophorolipid amides | $R^3 = CH_2CH_2NMe_2$ | 30 |
| | $R^3 = CH_2CH_2NMe_3^+$ | 31 |
| Sophorolipid biogenic amides | $R^3 = (CH_2)_5NH_2$ | 32 |
| | $R^3 = (CH_2)_4NH(CH_2)_3NH_2$ | 33 |
| | $R^3 = (CH_2)_3NH(CH_2)_4NH-(CH_2)_3NH_2$ | 34 |
| | $R^3 = CH_2CH_2$-(1-Imidazole) | 35 |
| | $R^3 = CH_2CH_2$-(m,p-benzenediol) | 36 |
| | $R^3 = CH_2CH_2$-(1-indole) | 37 |
| | $R^3 = CHOHCH_2$(p-phenol) | 38 |
| Sophorolipid cross metathesis products | R = Methyl | 39 |
| | R = Ethyl | 40 |
| | R = Butyl | 41 |
| | R = Hexyl | 42 |
| | R = Lauryl | 43 |

TABLE 1-continued

Modified Sophorolipids (MSLs) and sophorolipid components of the natural mixture incorporated for use in this invention. The hydroxylated fatty acid of the natural mixture is predominantly 17-hydroxyoleic acid.

| Class/Structure | Substituent(s) | Code |
|---|---|---|
| Short chain SL ethyl ester | | 44 |

TABLE 2

CMC values for SL-amides (from this invention) SL-esters (from earlier publication in *Colloids and surfaces*, 2004, 240, 75).

| Compound codes | Compound name | CMC Range ($10^{-6}$M) | MST (mN/m) |
|---|---|---|---|
| 6 | SL-Methyl Ester | 95-100 | 38.4 |
| 7 | SL-Ethyl Ester | 36-40 | 37.5 |
| 8 | SL-Butyl Ester | 7-9 | 34.5 |
| 16 | SL-Hexyl Ester | 3-4 | 34.0 |
| 23 | SL-Ethyl Amide | 300-310 | 40.9 |
| 22 | SL-Methyl Amide | 650-670 | 43.3 |
| 24 | SL-Butyl Amide | 45-50 | 38.7 |
| 25 | SL-Hexyl Amide | 29-32 | 36.5 |

*CMC: Critical micelle concentration, M: moles, MST: minimum surface tension

TABLE 3

Solubility for SL-amides (compounds 22, 23, 24 and 25), SL-esters (compounds 6, 7, 8 and 16), natural SLs (compounds 1, 2 and 3) and SDS.

| Compound Codes | Compound name | Solubility (mg/mL) |
|---|---|---|
| 6 | SL-Methyl Ester | <1 |
| 7 | SL-Ethyl Ester | <3 |
| 8 | SL-Butyl Ester | <3 |
| 16 | SL-Hexyl Ester | <5 |
| 22 | SL-Methyl Amide | >60 |
| 23 | SL-Ethyl Amide | >40 |
| 24 | SL-Butyl Amide | >40 |
| 25 | SL-Hexyl Amide | <11 |
| 3 | Acidic SL | >50 |
| 2 | Lactonic SL | <5 |
| 1 | Natural SL | <10 |
| | SDS | >100 |

TABLE 4

Average droplet size determined by a Coulter LS 230 analyzer for paraffin oil-to-water (7:3 v/v) 24 hours after preparation stored at room temperature (25° C.).

| Concentration (weight %) | SL-Butyl Amide (24) Size (μm) | SL-Hexyl Amide (25) Size (μm) | SL-Butyl Ester (8) Size (μm) | SL-Hexyl Ester (16) Size (μm) | SDS Size (μm) |
|---|---|---|---|---|---|
| 0.5 | 3.0 ± 0.2 | 2.7 ± 0.4 | 2.5 ± 0.3 | 2.3 ± 0.4 | 2.3 ± 0.2 |
| 1 | 2.5 ± 0.2 | 2.7 ± 0.2 | 2.4 ± 0.3 | 2.1 ± 0.3 | 2.1 ± 0.1 |
| 2 | 1.9 ± 0.1 | 1.7 ± 0.1 | 1.7 ± 0.1 | 1.7 ± 0.2 | 1.6 ± 0.2 |

TABLE 5

Average droplet size determined by a Coulter LS 230 analyzer for paraffin oil-to-water (7:3 v/v) emulsions aged for 3-months at room temperature (25° C.).

| Concentration (weight %) | SL-Butyl Amide (24) Size (μm) | SL-Hexyl Amide (25) Size (μm) | SL-Butyl Ester (8) Size (μm) | SL-Hexyl Ester (16) Size (μm) | SDS Size (μm) |
|---|---|---|---|---|---|
| 0.5 | 6.3 ± 1.0 | 4.0 ± 0.4 | 3.5 ± 0.4 | 2.9 ± 0.2 | 3.1 ± 0.1 |
| 1 | 4.7 ± 0.8 | 3.7 ± 0.7 | 3.1 ± 0.5 | 2.5 ± 0.1 | 2.7 ± 0.1 |
| 2 | 3.0 ± 0.4 | 2.2 ± 0.5 | 2.1 ± 0.4 | 1.9 ± 0.1 | 2.0 ± 0.1 |

TABLE 6

Lemon oil solubilization by SL-hexyl ester (16), SL-octyl ester SL (17), SL-dodecyl ester (18), TWEEN ® 60 and Rhamnolipid.

| Compound Code | lemon oil/water volume ratio | Sonication Time (sec) | Surfactant Concentration (weight-%)[a] | Emulsion aging time | Emulsion Droplet Size (nm)[b] |
|---|---|---|---|---|---|
| 16 | 1/99 | 60 | 0.25 | 1 Week | 200 |
|  |  |  |  | 1 Month | 138 |
|  |  |  | 1 | 1 Week | 22 |
|  |  |  |  | 1 Month | 52 |
|  |  | 120 | 0.25 | 1 week | 149 |
|  |  |  |  | 1 Month | 105 |
|  |  |  | 0.5 wt % | 1 Week | 255 |
|  |  |  |  | 1 Month | 287/82 |
|  |  |  | 1 | 1 Week | 20 |
|  |  |  |  | 1 Month | 26 |
|  | 5/95 | 60 | 0.25 | 1 week | 330 |
|  |  |  |  | 1 Month | 506/177 |
|  |  |  | 1 | 1 Week | 313/112 |
|  |  |  |  | 1 Month | 471/32 |
|  |  | 120 | 0.25 | 1 week | 325 |
|  |  |  |  | 1 Month | 450/166 |
|  |  |  | 0.5 | 1 Week | 320/29 |
|  |  |  |  | 1 Month | 505/120 |
|  |  |  | 1 | 1 Week | 336/246 |
|  |  |  |  | 1 Month | 518/25 |
| 17 | 1/99 | 60 | 1 | 2 Days | 52 |
|  |  | 60 | 1 | 1 Week | 92 |
|  |  | 60 | 1 | 5 Weeks | 183 |
|  | 5/95 | 60 | 1 | 2 Days | 167 |
|  |  | 60 | 1 | 1 Week | 179 |
|  |  | 60 | 1 | 5 Weeks | 325 |
| 18 | 1/99 | 60 | 1 | 1 Week | 238 |
|  |  | 60 | 1 | 5 Weeks | 277 |
|  | 5/95 | 60 | 1 | 1 Week | 389/327 |
|  |  | 60 | 1 | 5 Weeks | 551/208 |
| TWEEN ® 60 | 1/99 | 120 | 1 | 1 Week | 173 |
|  | 1/99 | 120 | 1 | 1 Month | 233 |
| Rhamnolipid | 1/99 | 120 | 1 | 1 Week | 379 |

[a] concentration of surfactant is calculated on a w/w basis relative to the mass of water used.
[b] performed by dynamic light scattering

TABLE 7

Crude oil clearing/displacement activity of MSLs.

| Surfactants | Louisiana Crude | Arabian Light Crude | Prudhoe Bay Crude |
|---|---|---|---|
|  | Oil displacement activity (in cm) | | |
| SL-methyl ester (6) | 6.5 ± 0.4 | 5.5 ± 0.1 | 6.9 ± 0.1 |
| SL-ethyl ester (7) | 6.3 ± 0.9 | 6.5 ± 0.2 | 6.6 ± 0.7 |
| SL-butyl ester (8) | 8.7 ± 0.35 | 6.7 ± 0.14 | 7.5 |
| Triton X-100 | 5.5 ± 0.21 | 6.05 ± 0.07 | 7.8 ± 0.07 |
| SDS | 0.5 ± 0.14 | 0.65 ± 0.21 | 1.2 ± 0.42 |
| Distilled water | 0.1 | 0.2 | 0.1 |

TABLE 8

Crude oil emulsification activity of MSLs.

| Surfactants | Louisiana Crude | Arabian Crude | Prudhoe Crude |
|---|---|---|---|
|  | Emulsification activity ($D_{610}$) | | |
| SL-ethyl ester (7) | 0.42 | 0.91 | 0.32 |
| SL-butyl ester (8) | 1.50 | 1.77 | 1.58 |
| NSL (1) | 0.13 | 0.13 | 0.05 |
| Triton X-100 | 0.28 | 0.17 | 0.49 |

REFERENCES

1. Stanghellini, M. E., D. H. Kim, S. L. Rasmussen and P. A. Rorabaugh. 1996. Control of root rot of peppers caused by *Phytophthora capsici* with a nonionic surfactant. Plant Dis. 80:1113-1116.

2. Stanghellini, M. E., R. M. Miller. 1997. Biosurfactants: their identity and potential efficacy in the biological control of zoosporic plant pathogens. Plant Dis. 81:4-12.

3. Yoo, D. S., B. S. Lee and E. K. Kim. 2005. Characteristics of microbial biosurfactant as an antifungal agent against plant pathogenic fungus. J. Microbiol. Biotechnol. 15(6): 1164-1169.

4. Bisht, K. S., R. A. Gross and D. L. Kaplan. 1999. Enzyme-mediated regioselective acylations of sophorolipids. J. Org. Chem. 64:780-789.

5. Trummler, K., Effenberger, F., Syldatk, C. 2003. An integrated microbial/enzymatic process for production of rhamnolipids and L-(+)-rhamnose from rapeseed oil with *Pseudomonas* sp. DSM 2874. Eur. J. Lipid Sci. Technol. 105, 563-571.

6. Marchal, R., Lemal, J., Sulzer, C. 1997. Method of production of sophorosides by fermentation with fed batch supply of fatty acid esters or oils, U.S. Pat. No. 5,616,479.

7. US Patent Publication No. 2008/0266036 A1. Microbial biosurfactants as agents for controlling pests.

8. Davila, A. M., R. Marchal, N. Monin, Vandecasteele, J. P. 1993. Identification and determination of individual sophorolipids in fermentation products by gradient elution high-performance liquid chromatography with evaporative light-scattering detection. J. Chromatography, 648, 139-149.
9. Asmer, H., Lang, S., Wagner, F., Wray, V. 1988. Microbial production, structure elucidation and biocon-version of sophorose lipids. J. Am. Oil Chem. Soc. 65, 1460-1466
10. Tulloch, A. P., Spencer, J. F. T., Gorin, P. A. J. 1962. Fermentation of long-chain compounds by *Torulopsis magnoliae*. I. Structures of the hydroxy fatty acids obtained by the fermentation of fatty acids and hydrocarbons. Can. J. Chem. 40, 1326-1338.
11. Zhou, Q. H., Klekner, V., Kosaric, N. 1992. Production of sophorose lipids by *Torulopsis bombicola* from safflower oil and glucose. J. Am. Oil Chem. Soc. 69, 89-91.
12. Zhou Q-H, Kosaric, N. 1995. Utilization of canola oil and lactose to produce biosurfactant with *Candida bombicola*. J. Am. Oil. Chem. Soc. 72, 67-71
13. Rau, U., Heckmann, R., Wray, V., Lang, S. 1999. Enzymatic conversion of a sophorolipid into a glucose lipid. Biotechnol. Lett. 21, 973-977
14. Felse, P. A., Shah, V., Chan, J., Rao, K. J., Gross, R. A. 2007. Sophorolipid biosynthesis by *Candida bombicola* from industrial fatty acid residues. Enzyme and Microbial Technology 40, 316-323.
15. Mueller, C. M., Viterbo, D., Murray, P. J., Shah, V.; Gross, R., Schulze, R., Zenilman, M. E., Bluth, M. H. 2006. Sophorolipid treatment decreases inflammatory cytokine expression in an in vitro model of experimental sepsis. Faseb Journal 20 (4): A204-A204 Part 1.
16. Shah, V., Doncel, G. F., Seyoum, T., Eaton, K. M., Zalenskaya, I., Hagver, R., Azim, A., Gross, R. A. 2005. Sophorolipids, microbial glycolipids with anti-human Immunodeficiency virus and sperm-immobilizing activities. Antimicrobial Agents and Chemotherapy 49, 4093-4100.
17. Zhang, L., Somasundaran, P., Singh, S. K., Felse, A. P., Gross, R. A. 2004. Synthesis and interfacial properties of sophorolipid derivatives. Colloids and Surfaces A: Physicochem. Eng. Aspects 240, 75-82.
18. Hagler, M., Smith-Norowitz, T. A., Chice, S., Wanner, S. R., Viterbo, D., Mueller, C. M. Gross, R.; Nowakowski, M.; Schulze, R.; Zenilman, M. E.; Bluth, M. H. 2007. Sophorolipids decrease IgE production in U266 cells by downregulation of BSAP (Pax5), TLR-2. STAT3 and IL-6. Journal of Allergy and Clinical Immunology, 119 (1), S263-S263
19. B. M. Irish, J. C. Correll and Morelock, T. E. 2002. The effect of synthetic surfactants on disease severity of white rust on spinach Plant Disease (2002) 86, 791-796.

The invention claimed is:
1. A method for producing a modified sophorolipid for use in dispersion, solubilization or emulsification processes, comprising the steps of:
   a) selecting a modified sophorolipid butyl or hexyl ester from the group consisting of the following formulas—:

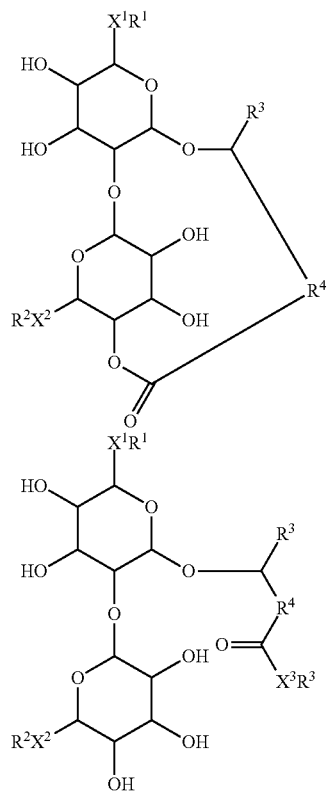

wherein:
   $X^1$ and $X^2$ are—oxymethyl (—$CH_2O$—);
   $R^1$ and/or $R^2$ are selected from the group of functional groups consisting of: hydrogen, acetyl, acryl, urethane, hydroxyalkyl, ether, and carboxyalkyl or alkyl containing heteroatoms (1°, 2°, and 3° amino, tetraalkylammonium, sulfate, phosphate);
   $R^3$ is a hydrogen or alkyl group;
   $R^4$ is an alkyl chain that has between 9 and 19 carbons and that has an unsaturation (C=C bond) at at least one site;
   $X^3$ contains heteroatoms; and
   the combination of $X^3R^3$ is selected from the group of functional groups consisting of hydroxy, alkanethiolate, amide, alkanamide, alkanamide containing heteroatoms, alkylsulfate, alkylphosphate, carbohydrate, and mono- or oligopeptide with 2-50 amino acids;
b) synthesizing the modified sophorolipid butyl or hexyl ester by a method using a natural sophorolipid produced by fermentation from a feedstock mixture; and
c) modifying the unsaturation (C=C bond) by a process selected from the group consisting of saturation by hydrogenation, epoxidization, hydroxylation by hydrolysis of the epoxide, hydroboration oxidation, dihydroxylation using osmium tetroxide, and conversion to a dithiirane, alkyl aziridine, cyclopropyl, or thioalkane derivative,
wherein the modified sophorolipid butyl or hexyl ester is used as at least one of an oil solubilizer, an emulsifier, a dispersant, and a surface active agent in a product selected from the group consisting of environmental, industrial, medical, personal care, cosmetics, and cleaning products.

2. The method of claim 1, wherein:
the environmental products are selected from the group consisting of oil spill cleaners, solubilizers, emulsifiers, dispersants, and surface active agents;
the industrial products are selected from the group consisting of oil effluent cleaners, tank cleaners, equipment cleaners, and oil solubilizers for industrial cleaning product formulations;
the medical products are selected from the group consisting of solubilizers for drugs, disinfectant formulations, and medical cleaning products;
the personal care and cosmetic products are selected from the group consisting of solubilizers, emulsifiers, dispersants and surface active agents for personal care products, lip balm, cleansing pads, deodorant, perfumes, fragrances, eye liner, facial tissue, lipstick, lotion, makeup, mouthwash, nail files, pomade, perfumes, razors, shampoo, conditioner, talcum powder, shaving cream, skin cream, toothpaste, hand wash liquids, skin care cleaning liquids, and disinfectants; and
the cleaning products are selected from the group consisting of solubilizers, emulsifiers, dispersants and surface active agents for household cleaning agents, dishwashing liquids, hand and body cleaning solutions, floor cleaning solutions, carpet cleaning solutions, detergents, washing liquids, and formulation of cleaning agents.

3. The method of claim 1, wherein the modified sophorolipid butyl or hexyl ester is obtained without purifying a reaction mixture or pure compounds of the modified sophorolipid derivative.

4. The method of claim 1, wherein the modified sophorolipid butyl or hexyl ester is obtained from sophorolipid mixtures of different purity with varying contents of natural to open chain sophorolipids.

5. The method of claim 1, wherein the modified sophorolipid butyl or hexyl ester acts synergistically to increase the solubilization, emulsification, dispersion, and surfactant activity relative to any of the components in the modified sophorolipid ester tested alone.

6. The method of claim 1, wherein the modified sophorolipid butyl or hexyl ester is used as a solution.

7. The method of claim 1, wherein the modified sophorolipid butyl or hexyl ester is in powder form and is used as a powder or dissolved in a solution prior to application.

8. The method of claim 1, further comprising the step of combining the modified sophorolipid butyl or hexyl ester with at least one of:
a buffering agent selected from the group consisting of natural buffers, organic and amino acids or their salts, citrate, gluconate, tartrate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof, phosphoric and phosphorous acids or their salts, and synthetic buffers;
a solubility control agent or excipient, to control the release of the active substances, selected from the group consisting of wax, chitin, chitosan, C12-C20 fatty acids, C12-C20 alcohols, amphiphilic esters of fatty acids with glycerol, glycol esters of fatty acids, C12-C20 amines, and amides of C12-C20 fatty acids;
a pH adjusting agent selected from the group consisting of potassium hydroxide, ammonium hydroxide, potassium carbonate or bicarbonate, hydrochloric acid, nitric acid, sulfuric acid, and mixtures thereof; and
a salt form of polyprotic acids.

9. The method of claim 1, further comprising using the modified sophorolipid butyl or hexyl ester by spraying, pouring, or dipping, wherein the modified sophorolipid butyl or hexyl ester is in a solution, a suspension, a powder, incorporated in wipes, papers or polymers.

10. The method as defined in claim 1, wherein the modified sophorolipid butyl or hexyl ester is formulated such that it is a solid formulation, wherein said solid formulation is formed into a shape.

11. The method of claim 1, wherein the modified sophorolipid butyl or hexyl ester is used for human or animal applications; is formulated as a formulation that is prepared in liquid, paste, ointment, suppository, capsule or tablet forms; and the formulation is encapsulated using components that protect the formulation from undesirable reactions and help the formulation resist adverse conditions in the environment or the treated object or body.

12. The method of claim 1, wherein the modified sophorolipid butyl or hexyl ester is applied to plants, pests, or soil.

13. The method of claim 1, wherein the modified sophorolipid butyl or hexyl ester is introduced directly in the soil in the vicinity of plant roots in the form of liquid, bait, powder, dusting, or granules, or alternatively, the biopesticidal compositions are inserted in the soil as tablets, spikes, rods, or other shaped moldings.

14. The method of claim 1, wherein the modified sophorolipid butyl or hexyl ester after formulation is a solid or semi-solid composition that is coated using film-coating compounds; wherein film coating protects a handler from coming in direct contact with an active ingredient in a formulation comprising the modified sophorolipid butyl or hexyl ester; and wherein a bittering agent is incorporated in the formulation.

15. The method of claim 1, wherein the modified sophorolipid butyl or hexyl ester is used in a quantity sufficient to act as an activity enhancer in antimicrobial, disinfectant, pesticidal, cleansing, personnel care, household cleaning, medical, and industrial formulations.

16. The method of claim 8, wherein the modified sophorolipid butyl or hexyl ester is used in a quantity sufficient to act as an activity enhancer in antimicrobial, disinfectant, pesticidal, cleansing, personnel care, household cleaning, medical, and industrial formulations.

17. The method of claim 1, wherein $R^4$ is an alkyl chain that has 15 carbons.

* * * * *